US007745592B2

(12) United States Patent
Massie et al.

(10) Patent No.: US 7,745,592 B2
(45) Date of Patent: Jun. 29, 2010

(54) CUMATE-INDUCIBLE EXPRESSION SYSTEM FOR EUKARYOTIC CELLS

(75) Inventors: Bernard Massie, Laval (CA); Alaka Mullick, Montreal West (CA); Peter C. K. Lau, Kirkland (CA); Yasuo Konishi, Kirkland (CA)

(73) Assignee: National Research Council of Canada, Ontario (CA)

( * ) Notice: Subject to any disclaimer, the term of this patent is extended or adjusted under 35 U.S.C. 154(b) by 963 days.

(21) Appl. No.: 10/135,362

(22) Filed: May 1, 2002

(65) Prior Publication Data

US 2004/0205834 A1 Oct. 14, 2004

Related U.S. Application Data

(60) Provisional application No. 60/287,418, filed on May 1, 2001.

(51) Int. Cl.
    *C07H 21/02*   (2006.01)
    *C07H 21/04*   (2006.01)
    *C12N 15/00*   (2006.01)
    *A01N 63/00*   (2006.01)
    *A01N 65/00*   (2009.01)

(52) U.S. Cl. ............... 536/23.1; 536/24.1; 536/24.2; 435/320.1; 424/93.1

(58) Field of Classification Search ............ 435/325, 435/320.1; 424/93.1; 514/44; 536/23.1, 536/23.4, 24.1

See application file for complete search history.

(56) References Cited

U.S. PATENT DOCUMENTS

| | | | |
|---|---|---|---|
| 5,362,646 | A | 11/1994 | Bujard et al. |
| 5,464,758 | A | 11/1995 | Gossen et al. |
| 5,589,362 | A | 12/1996 | Bujard et al. |
| 5,650,298 | A * | 7/1997 | Bujard et al. ............ 435/69.7 |
| 5,891,690 | A | 4/1999 | Massie |
| 5,972,650 | A | 10/1999 | Yao |

FOREIGN PATENT DOCUMENTS

WO     WO 96/01313     1/1996

OTHER PUBLICATIONS

Rudinger (1976) Peptide Hormones, University Park Press, Baltimore, MD., pp. 1-7.*
Bowie, et al. (1990) Science, 247 : 1306-10.*
Stryer (1988) Biochemistry, 3rd Ed., by Freeman and Co., New York, NY., pp. 809-813.*
Garrett and Grisham, "Transcription and the Regulation of Gene Expression" (1995) Biochemistry, 1st Ed., by Saunders College Publishing, Philadelphia, PA, p. 973.*
Kovacs, et al. (1986) Nucleic Acids Research, 14(6): 2429-42.*
Krohn, et. al. (1996) J. Biol. Chem., 271(39): 23884-94.*
Saenger, et al. (2000) Angew. Chem. Int. Ed., 39: 2042-52.*
Yoko Yoshida et al., *Adenovirus-Mediated Inducible Gene Expression through Tetracycline-Controllable Transactivator with Nuclear Localization Signal*, Biochemical and Biophysical Research Communications No. 230, pp. 426-430 (1997).
L. Nover, *Gene Technology and Functional Analyses of Heat Shock Genes*, Heat Shock Response, Chapter 6, pp. 167-220.
Feng Yao et al., *Tetracycline Repressor, tetR, rather than the tetR-Mammalian Cell Transcription Factor Fusion Derivatives, Regulates Inducible Gene Expression in Mammalian Cells*, Human Gene Therapy, No. 9. pp. 1939-1950, Sep. 1, 1998.
Nanette Mittereder et al., *Evaluation of the Concentration and Bioactivity of Adenovirus Vectors for Gene Therapy*, Journal of Virology, vol. 70, No. 11, pp. 7498-7509, Nov. 1996.
Bernard Massie et al., *Inducible Overexpression of a Toxic Protein by an Adenovirus Vector with a Tetracycline-Regulatable Expression Cassette*, Journal of Virology, vol. 72, No. 3, pp. 2289-2296, Mar. 1998.
Takashi Yamagami et al., *Complete Nucleotide Sequence of Human Vasoactive Intestinal Peptide/PHM-27 Gene and Its Inducible Promoter[a]*, Annals New York Academy of Sciences, vol. 527, pp. 87-102, 1988.
Michèle Sawadogo et al., *Interaction of a Gene-Specific Transcription Factor with the Adenovirus Major Late Promoter Upstream of the TATA Box Region*, Cell, vol. 43, pp. 165-175, Nov. 1985.
Antoine W. Caron et al., *Use of a micromanipulator for high-efficiency cloning of cells co-expressing fluorescent proteins*, pp. 137-145.
Peter F. Searle et al., *Building a Metal-Responsive Promoter with Synthetic Regulatory Elements*, Molecular and Cellular Biology, vol. 5, No. 6, pp. 1480-1489, Jun. 1985.
Agnes Jani et al., *Generation, validation, and large scale production of adenoviral recombinants with large size inserts such as a 6.3 kb human dystrophin cDNA*, Journal of Virological Methods, No. 64, pp. 111-124, 1997.
Steven L. McKnight et al., *Analysis of Transcriptional Regulatory Signals of the HSV Thimidine Kinase Gene: Identification of an Upstream Control Region*, Cell vol. 25, pp. 385-398, Aug. 1981.
Kelly E. Mayo et al., *The Mouse Metallothionein-I Gene Is Transcriptionally Regulated by Cadmium following Transfection into Human or Mouse Cells*, Cell, vol. 29, pp. 99-108, May 1982.
Bernard Massie et al., *New adenovirus vectors for protein production and gene transfer*, Cytotechnology No. 28, pp. 53-64, 1998.
Frank Lee et al., *Glucocorticoids regulate expression of dihydrofolate reductase cDNA in mouse mammary tumour virus chimaeric plasmids*, Nature, vol. 294, pp. 228-232, Nov. 19, 1981.
Gerd Klock et al., *Oestrogen and glucocorticoid responsive elements are closely related but distinct*, Nature, vol. 329, pp. 734-736, Oct. 22, 1987.
Nancy E. Hynes et al., *Hormone-responsive expression of an endogenous proviral gene of mouse mammary tumor virus after molecular cloning and gene transfer into cultured cells*, Proc. Natl. Acad. Sci. USA, vol. 78, No. 4, pp. 2038-2042, Apr. 1981.

(Continued)

*Primary Examiner*—Robert M Kelly
(74) *Attorney, Agent, or Firm*—Ogilvy Renault LLP

(57) ABSTRACT

The invention relates to a new "gene-switch" (cumate-inducible switch) for mammalian cells. This switch is as useful in the development of expression systems and cell-based assays for functional genomics as in the generation of viral vectors for gene therapy.

16 Claims, 17 Drawing Sheets

OTHER PUBLICATIONS

Mickey C.-T. Hu et al., *The Inducible lac Operator-Repressor System Is Functional in Mamalian Cells*, Cell. vol. 48, pp. 555-566, Feb. 27, 1987.

Stanley M. Hollenberg et al., *Multiple and Cooperative Trans-Activation Domains of the Human Glucocorticoid Receptor*, Cell, vol. 55, pp. 899-906, Dec. 2, 1988.

Glenn R. Hicks et al., *Protein Import Into the Nucleus: An Integrated View*, Annu. Rev. Cell Dev. Biol., No. 11, pp. 155-188, 1995.

Manfred Gossen et al., *Tight control of gene expression in mammalian cells by tetracycline-responsive promoters*, Proc. Natl. Acad. Sci. USA, vol. 89, pp. 5547-5551, Jun. 1992.

Manfred Gossen et al., *Control of gene activity in higher eukaryotic cells by prokaryotic regulatory elements*, TIBS, No. 18, pp. 471-475, Dec. 1993.

Richard W. Eaton, *p-Cymene Catabolic Pathway in Pseudomonas putida F1: Cloning and Characterization of DNA Encoding Conversion of p-Cymene to—Cumate*, Journal of Bacteriology, vol. 179, No. 10, pp. 3171-3180, May 1997.

Myles Brown et al., *lac Repressor Can Regulate Expression from a Hybrid SV40 Early Promoter Containing a lac Operator in Animal Cells*, Cell, vol. 49, pp. 603-612, Jun. 5, 1987.

Ralph L. Brinster et al., *Regulation of metallothionein-thymidine kinase fusion plasmids injected into mouse eggs*, Nature, vol. 296, pp. 39-42, Mar. 4, 1982.

Helen M. Blau et al., *Tet B or not tet B: Advances in tetracycline-inducible gene expression*, Proc. Natl., Acad. Sci. USA, vol. 96, pp. 797-799, Feb. 1999.

Udo Baron et al., *Tetracycline-controlled transcription in eukaryotes: novel transactivators with graded transactivation potential*, Nucleic Acids Research, vol. 25, No. 14, pp. 2723-2729, 1997.

Klara Abravaya et al., *Heat Shock-Induced Interactions of Heat Shock Transcription Factor and the Human hsp70 Promoter Examined by In Vivo Footprinting*, Molecular and Cellular Biology, vol. 11, No. 1, pp. 586-592, Jan. 1991.

Wolfram Saenger et al., *The Tetracycline Repressor—A Paradigm for a Biological Switch*, Angew. Chem. Int. Ed., No. 39, pp. 2043-2052, 2000.

Martin Fussenegger, *The Impact of Mammalian Gene Regulation Concepts on Functional Genomic Research, Metabolic Engineering, and Advanced Gene Therapies*, Biotechnol. Prog. No. 17, pp. 1-51, 2001.

\* cited by examiner

Off (no cumate)
CymR
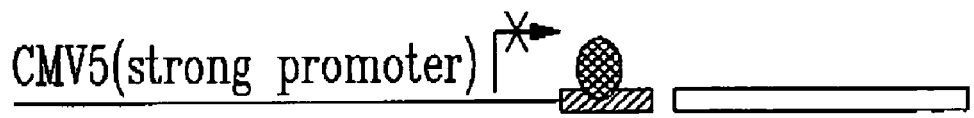
CuO    reporter
ON (cumate)
 CymR.cumate
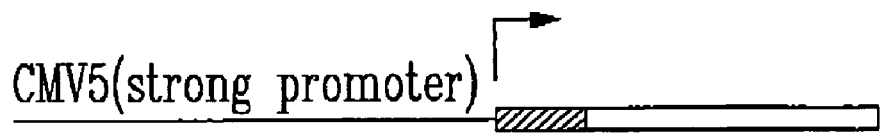
CuO    reporter

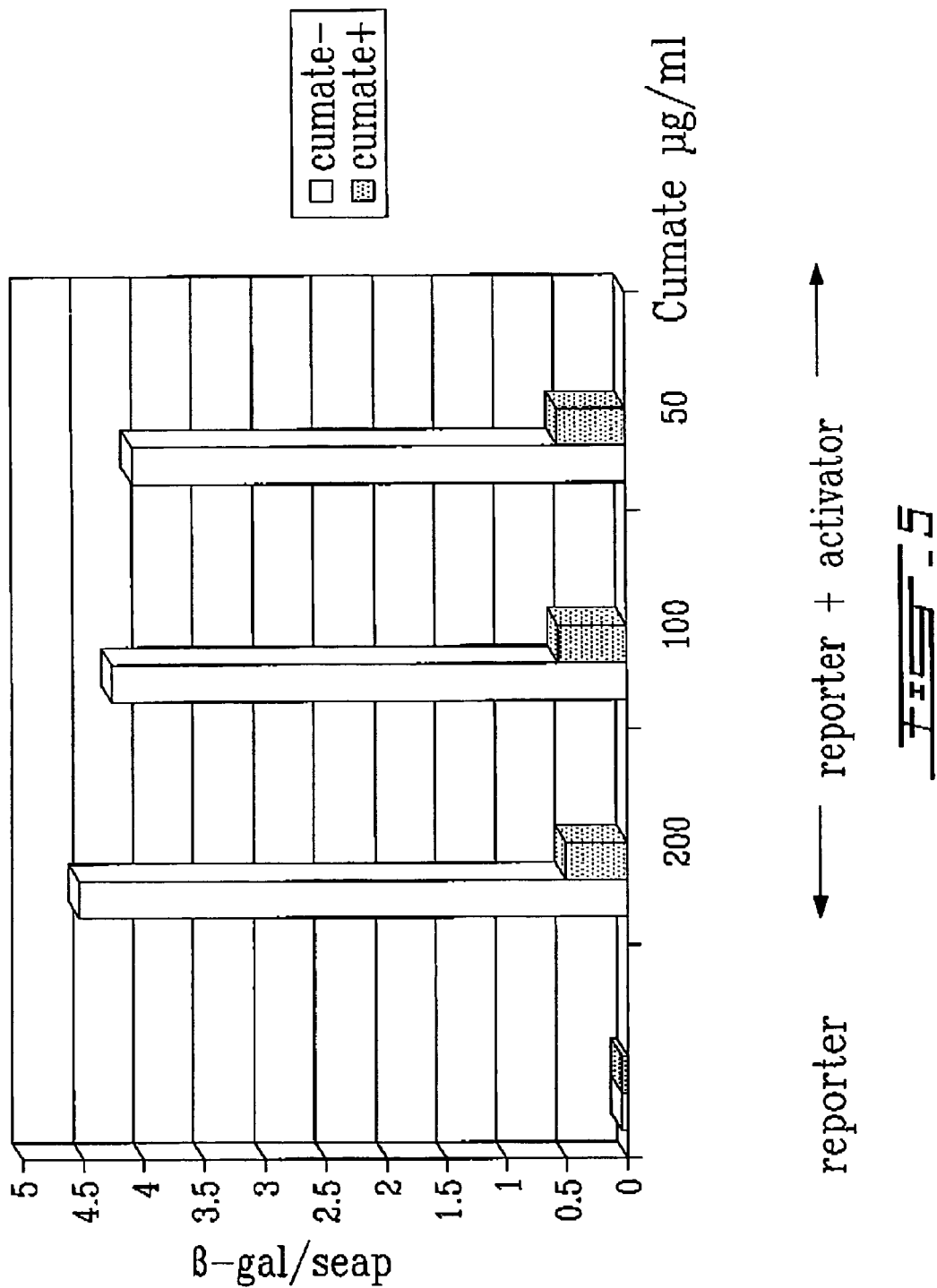

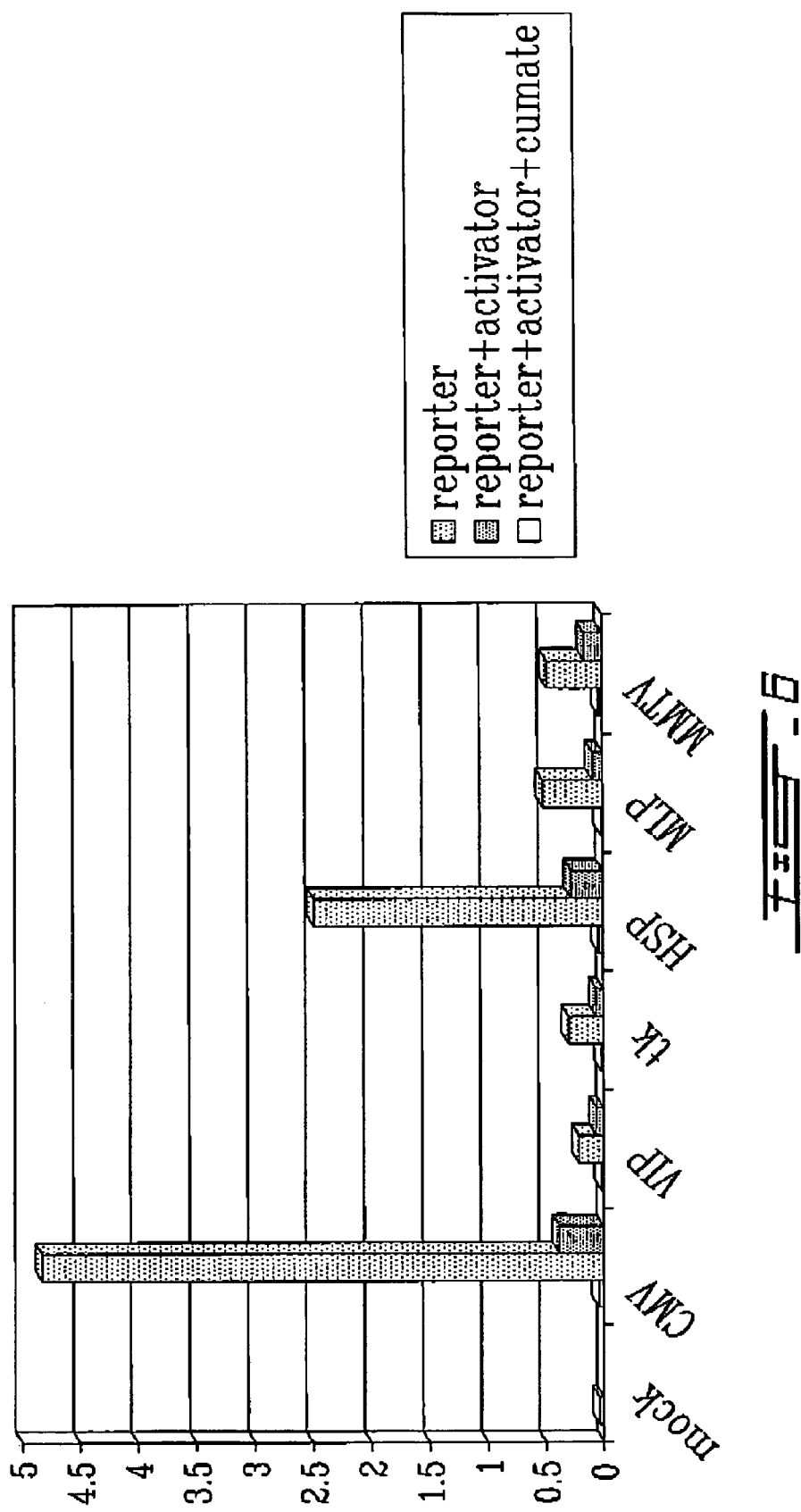

| sample | β-gal/seap | Fold repression |
|---|---|---|
| mock | 0 | |
| reporter | 0 | |
| reporter + activator (+nls) | 3.58 | |
| reporter + activator (+nls) +Cu | 0.38 | 9.4 |
| reporter + activator (-nls) | 3.26 | |
| reporter + activator (-nls) +Cu | 0.093 | 35 |

FIG. 7b

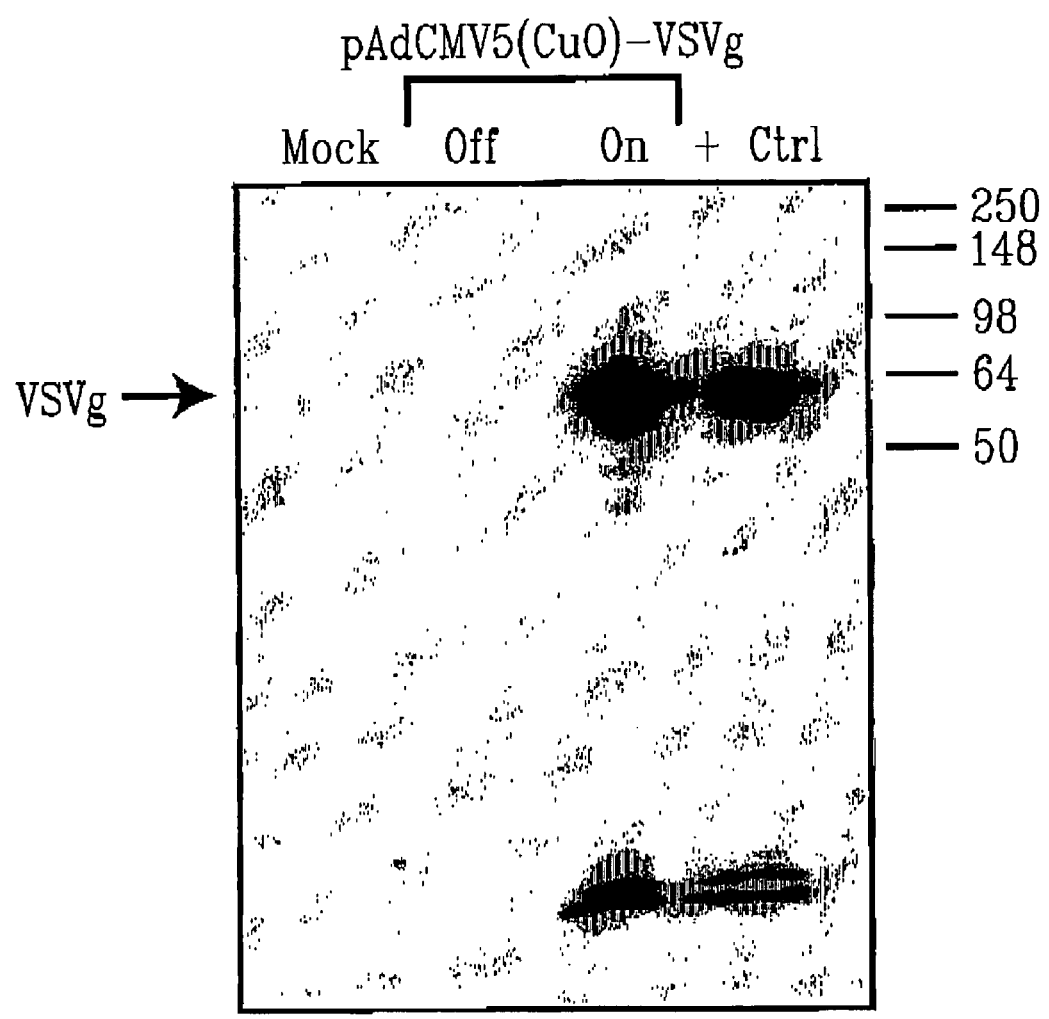

FIG. 14b ON
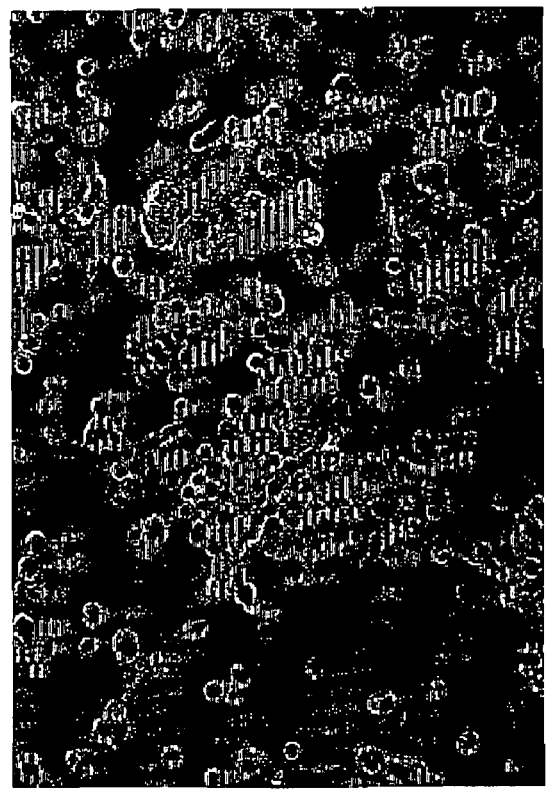
FIG. 14a OFF

On (GFP)

Off (GFP)

Off (phase contrast)

SEQUENCE LISTING

<160> NUMBER OF SEQ ID NOS: 2

<210> SEQ ID NO 1
<211> LENGTH: 76
<212> TYPE: DNA
<213> ORGANISM: Artificial Sequence
<220> FEATURE:
<223> OTHER INFORMATION: P1 promoter/operator containing sequence

<400> SEQUENCE: 1
attgactcag gagttttca gccggatgat cgcgacaaga aagaaacaaa ccaacctgtc    60
tgtattatct ccacag                                                  76

<210> SEQ ID NO 2
<211> LENGTH: 76
<212> TYPE: DNA
<213> ORGANISM: Artificial Sequence
<220> FEATURE:
<223> OTHER INFORMATION: P2-region

<400> SEQUENCE: 2
cttgacaggt gaattcgagg cggatgattt tttttgaaaa caaacagaca atctggtctg    60
tttgtattat aagtaa                                                   76

CUMATE-INDUCIBLE EXPRESSION SYSTEM FOR EUKARYOTIC CELLS

CROSS-REFERENCE TO RELATED APPLICATIONS

This application claims the benefit under 35 USC §119(e) of U.S. application Ser. 60/287,418 filed May 1, 2001.

BACKGROUND OF THE INVENTION (a) Field of the Invention

The invention relates to a new "gene-switch" (cumate-inducible switch) for mammalian cells. This switch is as useful in the development of expression systems and cell-based assays for functional genomics as in the generation of viral vectors for gene therapy.

(b) Description of Prior Art

Tightly controlled inducible expression of foreign proteins would greatly aid functional studies in heterologous systems. The ability to regulate both the level and the duration of expression would allow the study of proteins whose constitutive expression might not be tolerated by the cell. A number of inducible systems endogenous to mammalian cells involving regulation by heavy-metals (Brinster, R. L., et al. *Nature (London)* 296: 39-42, 1982; Mayo, E. K., et al. *Cell* 29: 99-108, 1982; and Searle, P. F., et al. *Molecular and Cellular Biology* 5: 1480-1489, 1985), steroid hormones (Hynes, N. E., N. Kennedy, et al. *Proc. Natl. Acad. Sci. USA* 78: 2038-2042, 1981; Lee, F., et al. *Nature (London)* 294: 228-232, 1981; and Klock, G., et al. *Nature (London)* 329: 734-736, 1987), heat shock ((Nouer, L. p.-., *Heat Shock Response*. Boca Raton, Fla., Ed. CRC, 1991) (reviewed in Mullick, A. and B. Massie *Encyclopedia of Cell Technology* pp. 1140-1164, 2000)) are widely used. However, a major limitation of these inducible mammalian promoters is the pleitropic effects of the inducers (heat shock, glucocorticoids etc.).

To overcome these problems, prokaryotic (Gossen, M., et al. *TIBS* 18: 471475, 1993) and insect regulatory systems (No, D., et al. *Proc. Natl. Aced. Sci. USA* 93: 3346-3351, 1996) have been adapted to construct gene switches that function in mammalian cells. Since inducer molecules are not expected to have targets in mammalian cells, the possibility of interference with cellular processes is reduced.

Of the prokaryotic proteins, two have proved particularly useful, the repressors from the lac (Brown, M., et at. *Cell* 49: 603-612, 1987; and Hu, M. C. -T. and N. Davidson *Cell* 48: 555-566, 1987) and the tet operons (Blau, H. M. and F. M. V. Rossi, *Proc. Natl. acad. sci. USA* 96: 797-799, 1999). Both have been incorporated in eukaryotic inducible expression systems using different strategies to control activation and repression of expression. Activation of expression is mediated by a chimaeric transactivator protein formed by the fusion of the bacterial repressor with an activation domain (Gossen, M. and H. Bujard, *Proc. Natl. acad. sci. USA* 89: 5547-5551, 1992, and Gossen, M., et al. *Science* 268: 1766-1769, 1995). The transactivator is able to activate transcription when bound to its DNA recognition sequence placed upstream of the minimal promoter. The ability of the activator to bind DNA is dependent on the presence/absence of the inducer molecule. Repression of expression is mediated by the repressor bound to operator sites placed downstream of the minimal promoter in the absence of inducer and repression is relieved on the addition of the inducer (Brown, M., et al. *Cell* 49: 603-612, 1987).

It would be highly desirable to be provided with an alternate activation/repression switch for expression of eukaryotic proteins.

SUMMARY OF THE INVENTION

One aim of the present invention is to provide a new switch for tightly controlled inducible expression of foreign proteins. Such new switch would greatly aid functional studies in heterologous systems. The ability to regulate both the level and the duration of expression would allow the study of proteins whose constitutive expression might not be tolerated by the cell. Of the prokaryotic proteins, two have proved particularly useful, the repressors from the lac and the tet operons.

For a number of applications it is essential to be able to express a protein in a heterologous system. Quite often it is desirable to regulate the duration and level of expression of the protein in question. It is not uncommon to be in a situation where the expression of the foreign protein is not well tolerated by the cell. In such cases the only way to generate a cell line or a recombinant viral vector that expresses this protein, is to use an inducible system, which is maintained in the off state at most times and expression is turned on only at the time of the experiment.

In accordance with the present invention there is provided a new "gene-switch" (cumate-inducible switch) for mammalian cells. This switch is as useful in the development of expression systems and cell-based assays for functional genomics as in the generation of viral vectors for gene therapy.

In accordance with the present invention there is provided a recombinant DNA molecule comprising:

a) a mammalian promoter sequence having a TATA element;

b) at least one CymR operator sequence positioned 3' to the TATA element; and c) a gene, such as for example a transactivator, lying 3' to said operator and operably linked to said promoter.

The promoter may be for example selected from the group consisting of CMV, VIP, tk, HSP, MLP, and MMTV promoters.

In accordance with one embodiment of the invention, there is provided a recombinant DNA molecule comprising a) a mammalian promoter sequence having a TATA element and b) a coding sequence of CymR operably linked to said promoter sequence.

Still in accordance with the present invention, there is provided a host cell transformed with a vector comprising the DNA molecule described above or infected with a virus containing the DNA molecule.

Further in accordance with the present invention, there is provided a method for producing recombinant protein in a mammalian cell, such as for example an embryonic stem cell, making the CymR repressor protein. The method comprises the steps of:

a) transforming said mammalian cell with a vector comprising:

i) a mammalian promoter sequence having a TATA element;

ii) at least one CymR operator sequence positioned 3' to the TATA element; and iii) a gene lying 3' to said CymR operator and operably linked to said promoter wherein said gene encodes said recombinant protein;

b) introducing an effector molecule that regulates CymR-mediated expression into the transformed cells of step a) to induce the expression of said gene and produce said recombinant protein.

The method may optionally further comprise prior to the introduction of the effector molecule the steps of:
a1) incorporating said stem cell into a blastocyst to form a chimeric embryo;
a2) implanting said chimeric embryo into a pseudopregnant animal;
a3) allowing said chimeric embryo to develop into a viable offspring;
a4) screening offspring to identify heterozygous animals expressing said gene; and
a5) breeding said heterozygous animals to produce homozygous transgenic animals producing said protein.

The effector molecule may for example be cumate, Dimethyl p-aminobenzoic acid (DM PABA), trimethyl cumate, and ethylbenzoate, or a salt thereof. The effector molecule may also be mainly para- or 4-substituted benzoate consisting of a bulky group of heteroatom, such a those selected from the group consisting of 3,4-dimethylbenzoate, 4-ethylbenzoate, 4-t-butylbenzoate, 4-phenylbenzoate, 4-benzylbenzoate, 4-ethoxybenzoate, 4-propyloxybenzoate, 4-n-butyloxybenzoate, 4-chlorobenzoate, 4-bromobenzoate, 4-iodobenzoate, 4-bromomethylbenzoate, 3,4-dichlorobenzoate, 4-trifluoromethylbenzoate, 4-ethyl-m-xylene, 4-vinyltoluene, 4-n-propyltoluene, 4-allyltoluene, 4-fluoro-p-toluate, 3-chloro-p-toluate, and 4-bromo-m-toluate. Analogues of cumate such as Benzoic acid (referred to as C1), p-methylbenzoic acid (referred to as C2), p-ethylbenzoic acid (referred to as C3), p-Propylbenzoic acid (referred to as C4), cumic acid (referred to as C5), p-isobutylbenzoic acid (referred to as C6), p-tert-butylbenzoic acid (referred to as C7), ibuprofen (referred to as C8), p-aminobenzoic acid (referred to as C9), p-N-methylaminobenzoic acid (referred to as C10), p-N-dimethylaminobenzoic acid (referred to as C11), p-N-methyl-N-ethylaminobenzoic acid (referred to as C12), and p-N-ethylaminobenzoic acid (referred to as C13) have also been tested.

In accordance with the present invention, there is also provided a recombinantly engineered virus comprising within its genome:
a) a recombinant promoter having a TATA element;
b) at least one CymR operator sequence positioned 3' to the TATA element; and
c) a gene lying 3' to said operator and operably linked to said promoter, wherein said gene inhibits the replication of said virus when expressed.

In accordance with the present invention, there is further provided a method for producing the virus described above. The method comprises the steps of:
a) growing said virus in a host expressing the CymR repressor protein; and
b) collecting and purifying the virus grown in step a).

Further in accordance with the present invention, there is provided a method for preparing a virus to serve as a vector, comprising:
a) engineering said virus to contain within its genome:
i) a recombinant mammalian promoter having a TATA element;
ii) at least one CymR operator sequence positioned 3' to the TATA element;
iii) a gene positioned 3' to said operator and operably linked to said promoter, wherein said gene encodes a protein capable of inhibiting the replication of said virus; and
iv) a nucleic acid therapeutic agent, such as an antisense inhibitor of gene expression or a nucleic acid coding for a protein with a therapeutic action, operably linked to a second promoter;
b) growing the virus prepared in step (a) in host cells expressing the CymR repressor protein; and
c) collecting and purifying the virus grown in step b).

Of course the recombinant protein made by host cell transformed with a vector comprising the DNA molecule described above or infected with a virus containing the DNA molecule is also intended to be part of the present invention.

The present invention also includes any transgenic animals made by the method described above.

In accordance with the present invention, there is also provided a transgenic animal having integrated into its genome a recombinant DNA comprising:
a) a mammalian promoter sequence having a TATA element;
b) at least one CymR operator sequence positioned 3' to the TATA element; and
c) a gene lying 3' to said operator and operably linked to said promoter.

The transgenic animal may further have a gene encoding the CymR repressor protein.

Also in accordance with the present invention, there is provided a recombinant protein made by such transgenic animals.

Further in accordance with the present invention, there is also provided a method for treating a patient for an infection by a first virus. The method comprises the steps of:
a) transforming a second virus by incorporating into its genome DNA comprising:
i) a mammalian promoter having a TATA element;
ii) at least one CymR operator sequence positioned 3' to the TATA element; and
iii) a gene positioned 3' to said operator and operably linked to said promoter, wherein said gene, when expressed, is capable of blocking the expression of both said first virus and said second virus;
b) growing the transformed second virus of step a) in a host expressing the CymR repressor protein;
c) collecting and purifying the second virus grown in step b); and
d) administering the second virus collected and purified in step c) to said patient.

Still in accordance with the present invention, there is also provided a method for delivering a nucleic acid therapeutic agent to cells. The method comprises the steps of:
a) preparing a virus to serve as a vector, wherein said virus is engineered to contain within its genome:
i) a recombinant mammalian promoter having a TATA element;
ii) at least one CymR operator sequence positioned 3' to the TATA element; and
iii) a gene positioned 3' to said operator and operably linked to said promoter, wherein said gene encodes a protein capable of inhibiting the replication of said virus;
iv) said nucleic acid therapeutic agent, operably linked to a second promoter;
b) growing the virus prepared in step a) in host cells expressing the CymR repressor protein;
c) collecting and purifying the virus grown in step b); and
d) administering the virus collected and purified in step c) to said patient.

In this later method, the virus may further comprise at least one CymR operator sequence lying 3' to a TATA element in said second recombinant promoter and 5' to said second recombinant gene.

In accordance with an alternate embodiment of the present invention, there is provided a recombinant DNA molecule comprising:
   a) mammalian promoter sequence having a TATA element
   b) at least one CymR operator sequence positioned 5' to the TATA element, and
   c) a gene lying 3' to the TATA element and operably linked to the promoter.

In its minimal form, the recombinant DNA molecule may only comprise:
   a) a mammalian promoter; and
   b) CymR-VP16 cumate activator coding sequences operably linked to the promoter.

Of course, as discussed previously, it is also intended to include in the present invention any recombinantly engineered virus that comprises within its genome the recombinant DNA molecule of the present invention.

For the purpose of the present invention the description that follows uses a number of terms that refer to recombinant DNA technology. In order to provide a clear and consistent understanding of the specification and claims, including the scope be given such terms, the following definitions are provided.

Viral vector: As used herein, "viral vector" and equivalent terms refer to viruses that are utilized for transferring selected DNA or RNA sequences into a host cell. The vectors maybe utilized for the purpose of transferring DNA into cells either in vitro or in vivo. Viruses that have been commonly used for the latter purpose include the retroviruses, adenoviruses, parvoviruses and herpes viruses.

Expression vector: This and comparable terms refer to a vector which is capable of inducing the expression of DNA that has been cloned into it after transformation into a host cell. The cloned DNA is usually placed under the control of (i.e., operably linked to) certain regulatory sequences such a promoters or enhancers. Promoters sequences maybe constitutive, inducible or repressible.

Substantially pure or purified: As used herein, "substantially pure" or "purified" means that the desired product is essentially free from contaminating cellular components. Contaminants may include, but are not limited to, proteins, carbohydrates and lipids. One method for determining the purity of a protein or nucleic acid is by electrophoresis in a matrix such as polyacrylamide or agarose. Purity is evidence by the appearance of a single band after staining.

Host: Any prokaryotic or eukaryotic cell that is the recipient of a vector is the host for that vector. The term encompasses prokaryotic or eukaryotic cells that have been engineered to incorporated a gene in their genome. Cells that can serve as hosts are well known in the art as are techniques for cellular transformation (see e.g., Sambrook, et al., Molecular Cloning: A Laboratory Manual, 2nd ed., Cold Spring Harbor (1989)).

Promotor: A DNA sequence that initiates the transcription of a gene. Promoters are typically found 5' to the gene and located proximal to the start codon. If a promoter is of the inducible type, then the rate of transcription increases in response to an inducing agent.

Expression: Expression is the process by which a polypeptide is produced from DNA. The process involves the transcription of the gene into mRNA and the translation of this mRNA into a polypeptide. Depending on the context in which used, "expression" may refer to the production of RNA, protein or both.

Recombinant: As used herein, the term "recombinant" refers to nucleic acid that is formed by experimentally recombining nucleic acid sequences and sequence elements. A recombinant host would be any host receiving a recombinant nucleic acid and the term "recombinant protein" refers to protein produced by such a host.

Operably linked: The term "operably linked" refers to genetic elements that are joined in such a manner that enables them to carry out their normal functions. For example, a gene is operably linked to a promoter when its transcription is under the control of the promoter and such transcription produces the protein normally encoded by the gene.

Nucleic acid therapeutic agent: This term refers to any nucleic acid sequence that directly, or indirectly, serves as a therapeutic agent. Typically, such agents will fall into two categories. The first category encompasses antisense nucleic acids that are designed to anneal to complementary sequences within the host cell, thereby inhibiting expression. Alternatively, the term may refer to nucleic acids that encode a therapeutic protein.

Operator (sequence): This term is used to refer to a short DNA sequence that interacts with a repressor protein. The operator is not only a defined sequence but also repressor-specific; these recognition sites in promoter regions are usually palindromes (perfect or imperfect repeats) of various lengths.

Gene: As used herein, "gene" refers to the nucleic acid sequence that undergoes transcription as the result of promoter activity. A gene may code for a particular protein or, alternatively, code for an RNA sequence that is of interest in itself, e.g. because it acts as an antisense inhibitor.

Mammalian promoter: The term "mammalian promoter" refers to promoters that are active in mammalian cells. Similarly, "prokaryotic promoter" refers to promoters active in prokaryotic cells.

BRIEF DESCRIPTION OF THE DRAWINGS

FIG. 3 is a schematic representation of the second strategy (strategy 2) according to another embodiment of the invention used to control gene expression;

FIG. 5 is a graph representing the effect of cumate concentration;

FIG. 6 is a graph representing the effect of the basal promoter sequence;

FIG. 7B is a Table representing the effect of nuclear localization signal in HeLa cells;

FIG. 12 is a graph representing rAd infection of 293-CymR clones:

FIG. 13 illustrates a microphaph showing the detection of VSVg expression with or without cumate addition;

FIGS. 14A and 14B represents micrographs showing the morphology of 293CymR cells infected with AdCMV5-CuO-VSVg when the switch of the present invention is off (FIG. 14A) or on (FIG. 14B);

DETAILED DESCRIPTION OF THE INVENTION

Figure 1:
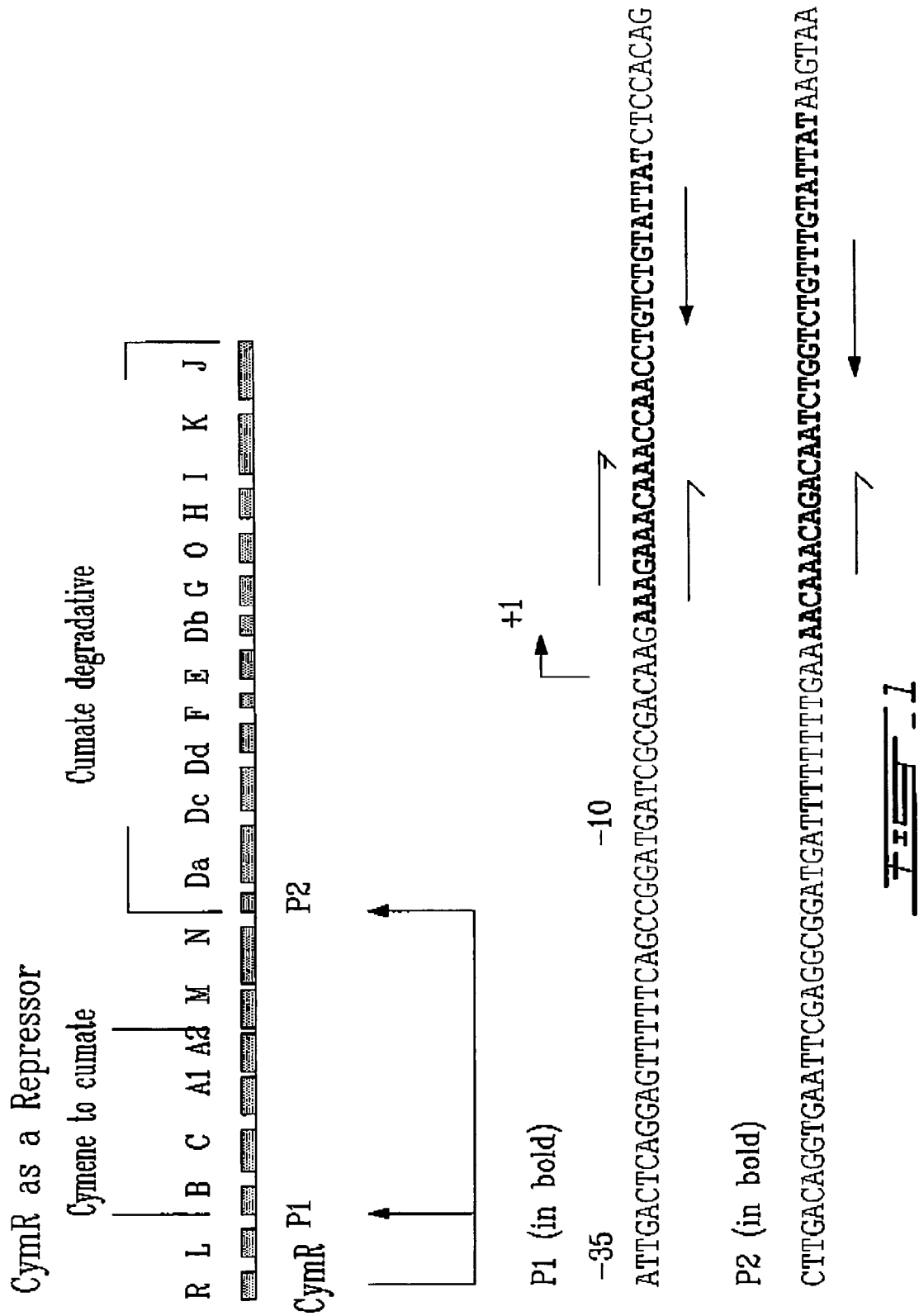
FIG. 1 is a schematic representation of the p-cym and p-cmt operons of *P. putida* showing also P1 (SEQ ID NO:1) and P2 (SEQ ID NO:2) operators.

The present invention is based upon the concept that it is possible to regulate mammalian gene expression using the tet operator and repressor protein.

In accordance with the present invention, there is described herein the construction of a new inducible system for expression in mammalian cells. The regulatory mechanism of a bacterial operon has been adapted to a mammalian expression system using two different strategies. One involves generating a chimaeric transactivator by fusing the bacterial repressor to an activation domain and since the DNA-binding ability of CymR is regulated by cumate binding, it is possible to regulate DNA-binding and hence trans-activation by the transactivator. The other strategy uses the CymR as a repressor, and again, since the presence or absence of cumate can regulate whether or not CymR will bind DNA, repression (in the absence of cumate) can be relieved by the addition of cumate.

The bacterial repressor chosen to use as a base for developing the system of the present invention controls expression from the p-cym operon in *Pseudomonas putida* (Eaton, R. W., *Journal of Bacteriology* 179: 3171-3180, 1997). It has a deduced molecular weight of 23,324. By sequence comparison, it has been proposed that the DNA-binding domain is in the N-terminus of the protein and has the characteristics of a helix-turn-helix motif. Sequence comparison of the promoter regions of the p-cym and p-cmt operons reveals an imperfect and a perfect inverted repeat respectively with characteristics of a binding site for a helix turn helix DNA-binding domain. The imperfect repeat which is located between the −35, −10 (s70) promoters and the beginning of the first gene cymB (encoding p-cumic alcohol dehydrogenase) in the pathway responsible for pcymene conversion to p-cumate has been defined as the operator sequence (P1). The P1 promoter/operator containing sequence is ATTGACTCAG GAGTTTTTCA GCCGGATGAT CGCGACAAGA AAGAAACAAA CCAACCTGTC TGTATTATCT CCACAG (SEQ ID NO:1). A similar sequence (a perfect repeat) is found in the promoter region of the Da gene, which is first in the degradative pathway of cumate. It has been called P2. The P2-region sequence is CTTGACAGGT GAATTCGAGG CGGATGATTT TTTTTGAAAA CAAACAGACA ATCTGGTCTG TTTGTATTAT AAGTAA (SEQ ID NO:2). Since CymR regulates expression from the p-cym and p-cmt operons, both P1 and P2 must be able to bind CymR. Furthermore, since P2 is a perfect repeat and P1 is not, one might expect that P2 would function better than P1. However, in assays conducted with strategy 1 described further, no significant difference was observed between the two sequences. Perhaps, the differences in the two halves of the imperfect repeat are not in critical bases. Moreover, in both cases six copies of the recognition sequence are used. Cooperative binding of several activator molecules to the multimerized site may overcome any little difference in binding activity to individual sites. Since p-cumate is the effector molecule that regulates the CymR-mediated expression and therefore CymR-DNA binding, p-cumate (and some derivatives thereof) was used to regulate expression from the mammalian expression system incorporating CymR. Furthermore, it does not appear to be toxic to mammalian cells at concentrations that can effectively regulate gene expression.

The need to solubilize p-cumate (p-cumic acid) in organic solvent (e.g. ethanol or dimethyl formamide) is a great disadvantage. The present invention thus provides water-soluble effectors as well as possibly expanding the spectrum of inducers beyond p-cumate. At first, cumic alcohol, 4-methyl benzylalcohol, ethyltoluene, indole-2-carboxylic acid, indole-3-carboxylic acid, benzoic acid, 3 and 4-hydroxybenzoic acids, 3,4-dihydroxybenzoic acid and 2,4-dihydrobenzoic acid were tried. Unfortunately none of these compounds could act as effective inducers. In this P2-cymlacZ fusion system, the threshold cumate concentration for induction is in the order of 0.002 millimoiar (mM).

Di-methyl p-aminobenzoic acid (DM PABA) and its sodium salt, DM PABA Na$^+$, Na$^+$cumate, Na$^+$trimethyl cumate, Na$^+$benzoate, Na+toluate, and Na+ethylbenzoate were tested as possible inducers at various concentrations. As a result, the water-soluble DM PABA (0.1 mM) was found just as good an inducer as parent cumate at the same concentration. Further experiments indicated that 0.02 mM of either DM PABA or DM PABA Na$^+$ are effective inducers. The sodium salt of cumic acid was also tested vs cumic acid (taken as cumate). The threshold of concentration giving a response did not change appreciably but the latter has the advantage of being water-soluble.

Na$^+$trimethyl cumate is an effective inducer at 0.1 mM, and Na$^+$ 4-ethylbenzoate also acts as an inducer. But despite their solubility, the response is evaluated as not as good as the parental cumate. Both sodium benzoate and sodium toluate are ineffective.

Other cumate derivatives were designed. Suitable cumate derivatives useful in accordance with the present invention, other than those already cited above, include mainly para- or 4-substituted benzoate consisting of a bulky group or heteroatom, such as 3,4-dimethylbenzoate, 4-ethylbenzoate, 4-t-butylbenzoate, 4-phenylbenzoate, 4-benzylbenzoate, 4-ethoxybenzoate, 4-propyloxybenzoate, 4-n-butyloxybenzoate, 4-chlorobenzoate, 4-bromobenzoate, 4-iodobenzoate, 4-bromomethylbenzoate, 3,4-dichlorobenzoate, 4-trifluoromethylbenzoate, 4-ethyl-m-xylene, 4-vinyltoluene, 4-n-propyltoluene, 4-allytoluene, 4-fluoro-p-toluate, 3-chloro-p-toluate, and 4-bromo-m-toluate.

This approach used in developing the present invention lends itself very well to improvement because of its modular nature. The repressor is fused to an activation domain, the two modules being functionally independent. It is possible thus to improve and exchange the activation domain without affecting repressor function. Modifications in the VP16 transactivation domain have been identified that render it less toxic, while maintaining its activation potential (Baron, U., et al. *Nucleic acids Research* 25: 2723-2729, 1997). It is similarly possible to modify the DNA-binding or dimerization properties of the repressor and leave the transactivation function unchanged. A number of such improvements have been described for the Tet system in the literature (reviewed in Blau, H. M. and F. M. V. Rossi, *Proc. Natl. acad. sci. USA* 96: 797-799, 1999).

A modification whose benefits are somewhat debatable relates to the use of the nuclear localization signal (nls). Reports in the literature are contradictory regarding the benefits of the addition of such a signal. In the original report of the development of the Tet switch, no difference was observed in the presence or absence of an nls sequence when the Tet switch was tested in transient transfection assays (Gossen, M., et al. *Science* 268: 1766-1769, 1995). Yoshida and Hamada (Yoshida and Hamada, *Biochem. Biophys. Res. Comm.*, 230:426-430, 1997), who use an adenoviral expression system, reported a huge benefit from the introduction of a nls in the transactivator expression plasmid. It was thus interesting to evaluate the effect of the nls in the system of the present invention. In transient transfection assays in several cell lines, the presence of the nls did not affect the ability of the transactivator to activate. However, on the addition of cumate, the 'off' value was not as low. Under normal circumstances a transcriptional transactivator would be expected to have a sequence that could direct its entry to the nucleus. The results obtained may thus seem somewhat surprising, except of course if the molecule contains a cryptic signal that is sufficient. Clearly the activator without the additional nls goes to the nucleus. Perhaps the presence of a very efficient nls is actually detrimental to the system since very large amounts of activator make it to the nucleus and cumate concentration is insufficient to saturate all activator molecules.

With respect to the second strategy too, addition of the nls was detrimental. Using the same amounts of expression plasmids in a transient transfection assay, the addition of the nls results in a less efficient repressor. Efficient transport to the nucleus would normally be considered essential for maximal occupation of the operator site and therefore the success of such a strategy. However addition of the nls results in lower DNA-binding ability. In EMSAs, equal amounts of extracts from cells transiently transfected with equal amounts of expression plasmids show a big difference in DNA-binding activity. Although amounts of CymR have not been confirmed by western analysis, it is unlikely although possible, that the nls sequence could destabilize the message or the protein. Nuclear localization sequences of this class (a single peptide region containing basic residues) (Hicks, G. R. and N. V. Raikhel *Annu. Rev. Cell Dev. Biol.* 11: 155-188, 1995) have been used successfully to target many other proteins to the nucleus. It is more probable that any change in the N-terminus of the protein affects DNA-binding, since the DNA-binding domain is in this part of the molecule.

The other component of the expression system that lends itself to modification is the minimal promoter element. Expression from this promoter element is activated by the binding of the cumate transactivator. Depending on the cell type in question and the minimal promoter being used, the level of the basal activity can vary quite dramatically. Depending on the application, it is possible to decide whether high induced levels or low basal levels are of paramount importance. By testing different minimal promoters in the cell line of choice it is possible to identify one that gives the best result in terms of a balance between low basal activity and high degree of activation. As seen in Table 1, the basal activity of the CMV min. promoter is 40-fold that of the mock sample in 293 cells whereas it is only 1.44-fold higher than the mock sample in HeLa cells.

TABLE 1

Basal Promoter Activity in 293 and HeLa Cells

| Sample | Basal activity | |
|---|---|---|
| | 293 | HeLa |
| Mock | 0.15 | 0.68 |
| CMV min. | 6.08 | 0.98 |
| VIP | 0.55 | 0.25 |
| Tk | 0.43 | 00.13 |
| HSP | 2.93 | 0.12 |
| MLP | 0.78 | 0.71 |
| MMTV | 1.08 | 0.23 |

In the second strategy where CymR is used as a repressor that reversibly blocks expression from a strong promoter, there is some debate in the literature as to the importance of the position of the operator site with respect to the start site. A detailed study by Hu and Davidson (Hu, M. C.-T. and N. Davidson *Cell* 48; 555-566, 1987) wherein lac operator sequences are inserted at different positions in the SV40 promoter region, indicate that in all cases there is a decrease in promoter activity due to the insertion per se. In the case of the CMV5 promoter, insertion in two different positions (between the TATA box and the initiation site or just downstream of the initiation site) did not affect expression. If anything there was a modest increase in the latter case. In support of the results obtained for the present invention, Yao et al. in U.S. Pat. No. 5,972,650 do not see any decrease in promoter activity as a result of the insertion of the tetracycline operator site. Yao et al. claim that they owe the success of the strategy to the positioning of the operator site. The positioning is such that the operator is 10 base pairs downstream of the TATA box, such that the repressor binds on the same side of the helix as the RNA polymerase and is therefore able to sterically block it most effectively. In the present invention however, operator sequences are placed further away from the TATA box (19 or 40 bases from the TATA) but they are able to mediate repression by the repressor very effectively. Since 19 and 40 bases corresponds to 1.8 and 2.2 turns of the helix the repressor should not be on the same face of the helix in both cases. Yet it is able to repress transcription just as effectively in the two configurations. Therefore, the positioning of the operator site should not be restricted to specific sites, as other sites may be found acceptable by one skilled in the art by simple routine testing. Perhaps CymR binds its operator sequence with exceptionally high affinity such that any disadvantage caused by sub-optimal placement is made up for by high occupancy of the site. It is also possible that CymR is able to interact with one of the components of the preinitiation complex with high enough affinity that position is not an overriding factor. Perhaps, in addition, it is easier to accumulate large amounts of CymR in a mammalian cell than some of the other bacterial repressors (Gossen, M., et al. *TIBS* 18: 471-475, 1993). High-level expression is important for the success of a repressor, since maximal occupancy of the operator site is essential for efficient repression.

The possibility that the cumate repressor is expressed to high levels in mammalian cells may also partly explain its success as a transactivator, when fused to an activation domain, especially in the context of the adenoviral system. Very low mois of the recombinant adenovirus expressing the activator result in dramatic increases in reporter activity. When compared to a constitutive promoter (CMV5) at the same moi (multiplicity of infection) as the cumate-responsive reporter, the activity of the CuA-driven promoter was a 100- fold higher than CMV5 when saturated for activator. This clearly indicates that the cumate activator is very potent. Taken together with the fact that very low mois of the activator virus are required to saturate the system, this system offers obvious benefits over the currently available expression systems for applications such as gene therapy where it is crucial to keep the viral load to a minimum. It is interesting to note that in the induced state, the Tet system is at best equivalent to the CMV5 promoter (Massie, B., et al. *Cytotechnology* 28: 53-64, 1998). Therefore it too would not compare favorably against the cumate system in terms of the maximal induced level at comparable mois of the activator virus. Keeping in mind the fact that both the Tet and the cumate activators are using the same transactivation domain (VP16), the high activation by the cumate system must be attributable to a) better expression levels of the activator for the same amount of template adenoviral DNA and/or b) higher affinity DNA recognition so as to facilitate activation of the preinitiation complex.

In *Pseudomonas putida* F1, the degradative pathway for p-cymene to its benzoate derivative p-cumate consists of 6 genes organized in an operon (cym) (Eaton, R. W., *Journal of Bacteriology* 179: 3171-3180, 1997). The cym operon is followed by the cmt operon that is responsible for the further degradation of cumate. The expression of the genes in both operons is regulated by a 28 kD repressor molecule (CymR) that binds operator sequences downstream of the start site of the promoter. CymR is in a DNA-binding configuration only in the absence of cymene or cumate, the effector molecules. This bacterial repressor protein was thus used and incorporated in a mammalian inducible system. Moreover two different strategies can be used to control expression with the effector molecule cumate.

The first strategy (strategy 1) consists of activating expression mediated by a chimaeric transactivator protein formed by the fusion of the bacterial repressor with an activation domain. The transactivator is able to activate transcription when bound to its DNA recognition sequence placed upstream of the minimal promoter.

The second strategy (strategy 2) consists of repressing expression mediated by the repressor bound to operator sites placed downstream of the minimal promoter in the absence of inducer whereby repression is relieved on the addition of the inducer.

In the present invention, the following plasmids have been used:

pAd CR 5 LacZ pAd CR5 LacZ was generated by removing the tet operator sequences from pAd TR5 LacZ and replacing them with the cumate operator sequences.

pAd TR5 LacZ pAdTR5F is a vector that contains seven repetitions of the Tet operator upstream of the minimal CMV promoter in a configuration that has been described before (Massie, B., et al. *J. Virol.* 72: 2289-2296, 1998). The multiple cloning site consists of 7 restriction endonucleases. It was digested with BgIII and KpnI. A PCR fragment was generated using a similar plasmid without the multiple cloning site, and the primers were designed so that the fragment was flanked by BamHI at the 5' end and KpnI at the 3' end. The 3' primer that contains the minimal promoter sequences had an AscI recognition sequence at the start site of transcription. The PCR fragment was cloned into BglII- KpnI-digested pAdTR5F resulting in the destruction of the BgIII site, the replacement of the multiple cloning site with a single cloning site (PmeI) and the introduction of AscI recognition sequence at the start site. A blunt ended fragment coding for the LacZ protein was cloned into the PmeI site.

To generate pAdCR5LacZ, pAdTR5 LacZ was digested with XhoI. The XhoI fragment (4527-5150) includes the Tet operator, minimal promoter and most of the Ad tripartite leader sequence. A PCR fragment containing the recognition sequence for HindIII at its 5' end, the minimal promoter element and the adenoviral tripartite leader sequence, was generated. The primers were designed such that the resulting fragment was flanked by XhoI sites and a new HindIII site was inserted. This intermediate vector was called pAdHindIIILacZ.

The 29 bp operator sequence P1 (FIG. 1) was repeated six times in a synthetic oligonucleotide. An annealing reaction was carried out with the complementary strand. The design of the two oligonucleotides was such that annealing overhangs would be created that were compatible with a HindIII site. This double stranded DNA was then cloned into the HindIII site of pAdHindIIILacZ. In FIG. 1, The top panel: Explain that the black boxes indicate the order of the genes in the degradation pathway of p-cymene to p-cumate (genes B, C, A1 and A2) and p-cumate to tricarboxylic acids (TCA) cycle intermediates (genes Da, Dc, Dd, F, E, Db, G, H, I, K and J). The direction of transcription of all genes except L is in the same direction. The functions of open reading frames/genes L, M, N, and O are largely unknown. Gene R encodes CymR, a repressor that acts at the promoter/operator sequences (lower panel sequences) in the intergenic region of genes L and B (labeled P1), and N and Da (labeled P2) (indicated by upward pointed arrows).

In the two sequences shown in FIG. 1, the −10 and −35 sequences refer to the promoter sequences or recognition elements. The +1 indicates transcription start site and the arrows indicate the respective imperfect repeat or perfect repeat of the two operator sequences.

pAd CR5' LacZ

The same cloning strategy was used to generate pAd CR5' LacZ except that the P2 operator sequence (FIG. 1) was multimerized instead of P1.

pAdCR6LacZ, pAdCR7LacZ, pAdCR8LacZ, pAdCR9LacZ and pAdCR10LacZ

The basal promoter in pAdCR5 LacZ has been derived from the CMV immediate early gene (−53 to +75 of the CMV IE gene promoter) (Gossen, M. and H. Bujard, *Proc. Natl. acad. sci. USA* 89: 5547-5551, 1992). In the process of generating pAdCR5 LacZ, an AscI site was introduced at the +1 position of pAdCR5'LacZ. There exists a KpnI site at position −72 of pAdCRLacZ such that the AscI-KpnI fragment encompasses the TATA box. The AscI-KpnI fragment of pAdCR5LacZ was replaced with AscI-KpnI fragments containing the TATA box from the herpes simplex virus thymidine kinase gene (tk) (McKnight, S. L., et al., *Cell* 25: 385-398, 1981) in pAdCR6LacZ, the adenoviral major late promoter (MLP) in pAdCR7LacZ (Sawadogo, M. and R. G. Roeder *Cell* 43: 165-175, 1985), the mouse mammary tumor virus LTR (MMTV) (Hollenberg, S. M. and R. M. Evans *Cell* 55: 899-906, 1988) in pAdCR8LacZ, the human heat shock promoter (HSP) (Abravaya, K., et al., *Moi. Cell. Biol.* 11: 586-592, 1991) in pAdCR9LacZ and the human vasoactive intestinal peptide gene (VIP) in pAdCRIOLacZ (Yamagami, T., et al. *Annals New York Academy of Sciences* 527: 87-102, 1988).

pAd cTAI

Oligonucleotides were designed to perform a PCR reaction on the CymR coding sequence such that the initiator methionine was in the context of a kozak sequence and was followed by the nuclear localization sequence (nls) MPKRPRPS (Gossen, M., et al. *Science* 268: 1766-1769, 1995). Furthermore, the resulting fragment had a BgIII site at its 5' end and a NotI site at its 3' end. An extra base was added at the 3' end to ensure that the fusion would stay in frame. Similarly oligonucleotides were designed to perform a PCR reaction on amino acid 363 to 490 of the herpes simplex virus virion protein 16 (VP16) such that the resulting fragment was flanked by NotI at the 5' end and BgIII at the 3' end. The two PCR fragments were cloned into pAdCMV5 K7 BFP (Massie, B., et al. *Cytotechnology* 28: 53-64, 1998) digested with BgIII and PmeI in a three-way ligation to create an expression vector wherein the CMV5 promoter was driving the expression of the fusion protein CymRVP16.

pAd cTAI (-nls)

Oligonucleotides were designed to perform a PCR reaction on CymR such that the initiator methionine was in the context of a kozak sequence and was immediately followed by the second amino acid of the CymR. The resulting fragment was flanked by BgIII on its 5' end and NotI on its 3' end. The nls containing BgIII-NotI fragment in pAd cTAI was replaced by the BgIII-PmeI fragment described here that encodes the CymR coding sequence without the nls.

pAdCMV5-Og-LacZ

A unique AgeI site was introduced in the promoter region of the CMV minimal promoter such that the site was 10 bases downstream of the TATA box using a PCR-based approach. A KpnI-AscI fragment encompassing the TATA box was amplified such that the reverse primer contained the sequence for an AgeI site. The KpnI-AscI fragment of pAdCR5'LacZ was replaced with the PCR fragment containing the AgeI site giving rise to pAdCr5' LacZ-AgeI.

A 469 by fragment corresponding to the promoter-enhancer region of CMV5 (−53 to −522) was amplified by PCR using pAd CMV5 K7 BFP (Massie, B., et al. *Cytotechnology* 28: 53-64, 1998) as the template. pAd CR5'LacZ-AgeI was digested with HindIII to remove the P2 operator elements and the CMV5 PCR fragment was cloned as a HindIII fragment to generate pAdCMV5LacZ-AgeI. Complementary oligonucleotides were designed such that the ends of the annealed molecule were compatible with sticky end ligation in a AgeI-digested vector. The oligonucleotide contained one copy of the cumate operator sequence (P2) (FIG. 1). The double-stranded molecule was cloned into AgeI site of pAdCMV5-Og-LacZ. The AgeI site is 9 bp downstream of the TATA box.

pAdCMV5-Os-LacZ pAdCR5LacZ was digested with HindIII to remove the P2 operator elements and the 469 bp CMV5 promoter-enhancer PCR fragment (described above) was cloned into the HindIII site to give rise to pAdCMV5LacZ. Complementary oligonucleotides were designed such that the ends of the annealed molecule were compatible with sticky end ligation in a AscI-digested vector. The oligonucleotide contained one copy of the cumate operator sequence (P2) (FIG. 1). The double-stranded molecule was cloned into AscI site of pAdCMV5LacZ. The Asc1 site is at the start site of transcription.

PAdCymR pAdCuI was digested with PmeI and NotI to release a fragment corresponding to the VP16 activation domain. The NotI site was rendered blunt with T4 DNA polymerase and the vector was religated giving rise to pAdCymR.

pAdCymR(-nls)

The same strategy that was described for generating pAdCymR was used except that pAdCuA(-nls) was used as the starting vector.

pAdcTA2(-nls)

pAdcTAI (-nls) was digested with BgIII and PmeI. The fragment coding for cTA2(-nls) was rendered blunt with T4 DNA polymerase and cloned into pAdCMV5DCBFPq (Massie, B., et al. *Cytotechnology* 28: 53-64, 1998) that had been digested with BgIII and rendered blunt with T4 DNA polymerase.

pAdCR5'GFP pAdCR5'GFP was generated from pAdTR5GFPq by exchanging the Tet-regulated promoter for the cumate-regulated promoter (AflII-BlpI fragment). pAdTR5GFPq was generated by cloning a BamHI fragment containing the coding sequence for GFPq in the unique BamHI site of pAdTR5F (Massie, B., et al. *Cytotechnology* 28: 53-64, 1998)

Cells and Transient Transfection

HeLa, 293 and BMAd78-42 were maintained in DMEM supplemented with 5% heat-inactivated FBS and 2 mM glutamine.

Transient transfections in 293 and HeLa cells were carried out using the calcium phosphate technique. One (1) ml of DNA-calcium phosphate precipitate contained 5 µg reporter, 250 ng activator/repressor (unless mentioned otherwise) and 3 µg seap in a total of 10 µg DNA. This was divided equally between two 60 mm plates, each containing $10^6$ 293 cells. One of the two plates received in addition 200 µg/ml cumate. Transient transfections in BMAD78-42 were carried out using Geneporter™ according to manufacturers directions. Briefly, 3 µg DNA (2 µg reporter, 25 ng transactivator and 0.5 µg seap) in 500 µl DMEM was added to $6\times10^5$ BMAd78-42 cells in DMEM. After 3 h 1 ml DMEM supplemented with 20% serum was added to the plates. Half the samples received DMEM supplemented with 20% serum and 400 µg/ml cumate.

Measurement of Seap and β-gal activity Seap activity was measured in 50 µl of cell culture medium by adding 50 µl of 2× seap buffer (1M diethanolamine PH 9.8, 2 mM $MgCl_2$, 10 mM 1-homoarginine and 20 mM p-nitrophenyl phosphate, disodium, hexahydrate Sigma 104 phosphatase substrate) and incubating at room temperature. $OD_{405}$ was read using a plate reader at different intervals. This information was used to ensure that the enzyme activity was measured under conditions where the substrate was in excess. β-galactosidase activity was measured in transfected cell extracts. Cells were lysed 48 h post-transfection by three freeze-thaw cycles in 0.25 M Tris.Hcl pH8. The cell lysate was centrifuged at 14,000×g and enzyme (β-galactosidase) activity was measured in the supernatant (cell extract) using a colorimetric assay containing 1 mM $MgCl_2$, 0.9 mg/ml ONPG, and 66 mM sodium phosphate (pH 7.5). Reactions were incubated at 37° C. until a faint yellow color had developed. $OD_{420}$ was measured at regular intervals until the reaction appeared to plateau. To measure low level activity (basal activity in the absence of transactivation) a chemiluminescent substrate was used. The reaction was performed using a kit from Roche diagnostics according to the instructions of the manufacturer.

Virus Generation Plaque Purification and Amplification

Recombinant viruses were generated by in vivo homoiogous recombination between overlapping sequences of linearized transfer vectors and Ad5/ΔE1ΔE3 as described in Jani et al. (Jani et al., *Journal of virological methods*, 64; 111-124, 1997) and Massie, Mosser et al. (Massie, B., et al. *Cytotechnology* 28: 53-64, 1998). Briefly, on the appearance of viral plaques, positive identification of Ad recombinants was carried out in the following manner: Viral plaques were eluted in 1 ml of cell culture medium. After three freeze-thaw cycles to release viral particles from the cells, 200 µl of the eluate was used to infect 5×10$^4$ 293 cells to amplify the viral mini-stock by allowing one round of viral replication.

Identification of Recombinant Plaques

GFP expression was used to identify recombinants for the virus AdCR5'GFP. Plaques for activator virus Ad-cTA2(-nls), were tested in a co-infection strategy with AdCR5'GFP. Only plaques that could modulate reporter gene expression in a cumate-dependent fashion, were included for further purification.

Purification and Amplification

Positive clones were then plaque purified on BMAdE1 cells (clone 78) (Massie, B., et al. J. Virol. 72: 2289-2296, 1998). After three rounds of purification, selected viral clones were amplified on 3×10$^7$ 293 cells. The resulting viral stock was titred using the technique of plaque assay with modifications suggested by Mittereder et al., (Mittereder, N., et al., *J. Virol.* 70:7498-7509, 1996). pAdCMV5GFPq was used as a reference for promoter strength (Massie, B., et al. *Cytotechnology* 28: 53-64, 1998).

The present invention will be more readily understood by referring to the following examples, which are given to illustrate the invention rather than to limit its scope.

EXAMPLE I

Strategy 1

Components of the Switch

The Activator

Figure 2:
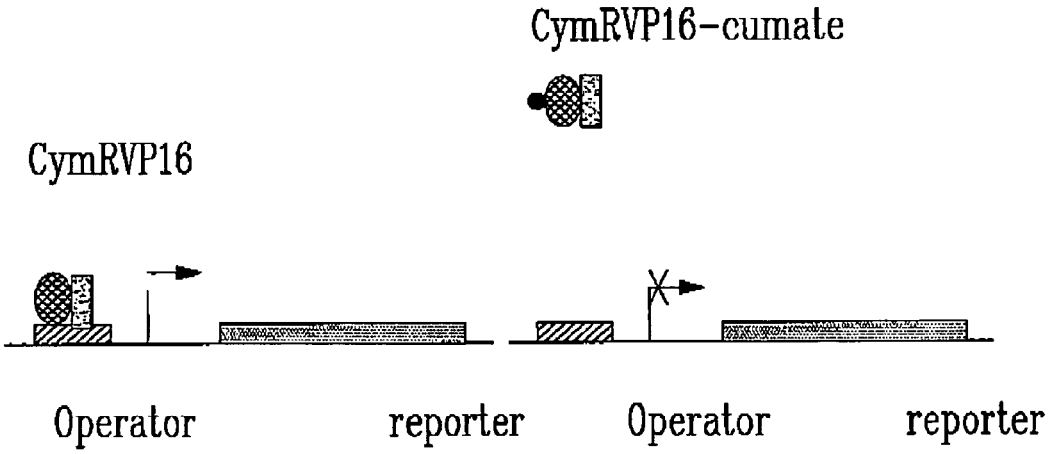
FIG. 2 is a schematic representation of the first strategy (strategy 1) according to one embodiment of the invention used to control gene expression.

A hybrid molecule (CymR-VP16) has been created that activates transcription once bound to DNA (FIG. 2).

The Reporter Construct

The reporter construct consists principally of three components: the CymR binding site (operator sequence), the basal promoter element and a reporter gene (β-galactosidase) such that the operator sequence is inserted upstream of the start site. (FIG. 2).

The Cumate Switch in 293 Cells

To test the system, reporter and activator constructs as described in Example I above, were co-transfected into 293 cells by the calcium-phosphate technique. A plasmid carrying the secreted alkaline phosphatase coding sequence under the control of a constitutive promoter was included in all transfections and seap activity in the cell culture medium was used to normalize for transfection efficiency.

Figure 4:
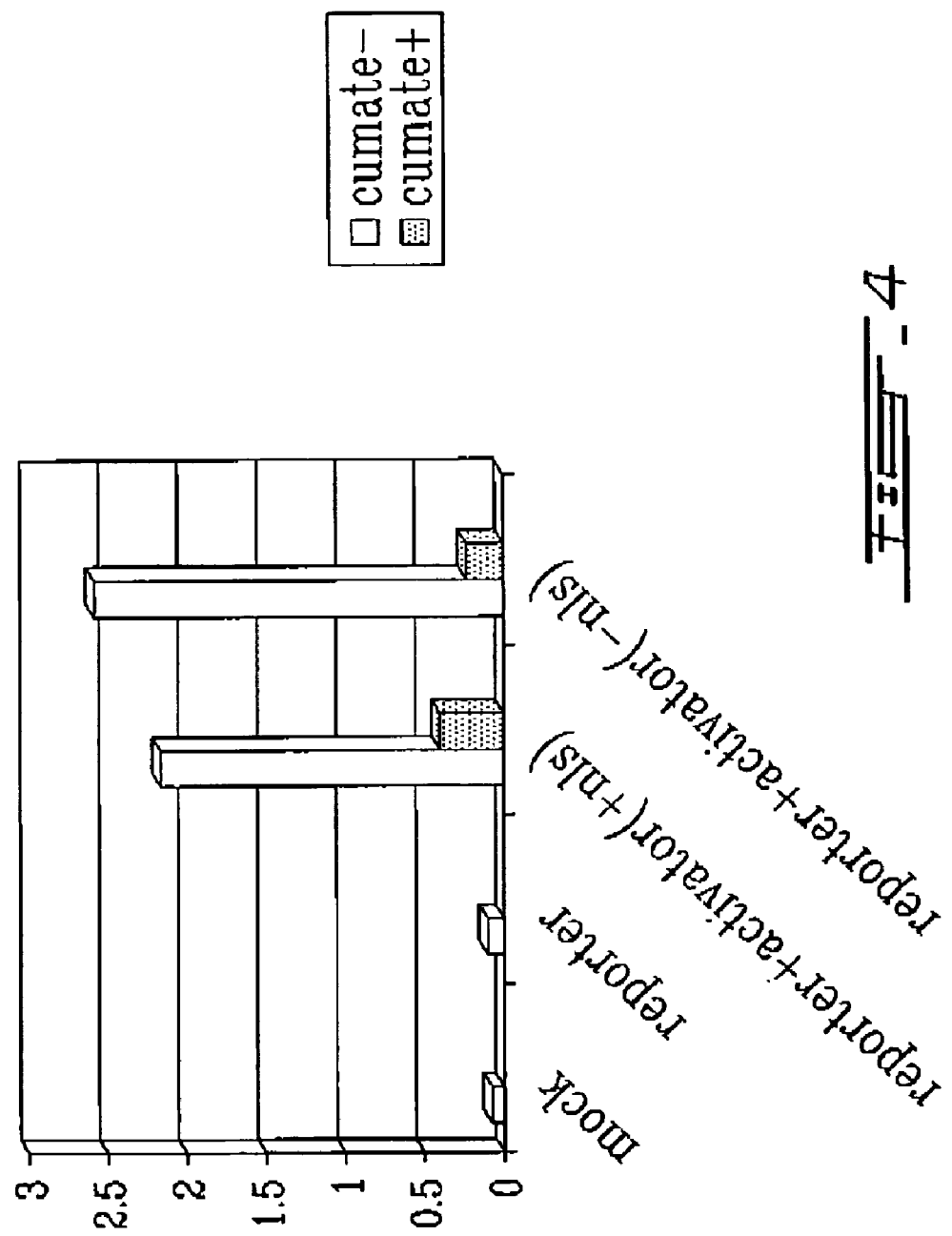
FIG. 4 is a graph representing the Cumate switch of the present invention in 293 cells.

FIG. 4 shows the results of a typical experiment. Reporter constructs (pAdCR5LacZ), when transfected alone produced minimal amounts of β-gal activity. On co-transfection with the plasmid coding for the transactivator (pAdcTA1(+nls)), however, there was a 10-fold increase in the activity of β-gal activity. Addition of cumate to the medium reduced the activation by 78%.

Effect of nls

Since there is some disagreement in the literature about the utility of the nls, the nls sequence was deleted from the expression vector and the resulting construct (pAdcTA1(-nls)) was used in experiments similar to the ones described above. Deletion of the nls sequence had no effect on the ability of the activator to activate transcription. In the presence of cumate, however, the reduction in activation was more efficient (89% reduction of the levels seen in the absence of cumate).

Effect of Cumate Concentration

The final concentration of cumate in the medium was 200 µg/ml. No visible effects on morphology or growth rates were observed when cells were grown in media containing 200 µg/ml cumate for a period of 4 weeks. However, the concentration of cumate can be reduced to 50 µg/ml with a minimal effect on the level of expression in the off state (reduction of 89% at 200 µg/ml, 87% at 100 µg/ml, 86% at 50 µg/ml cumate) (FIG. 5).

Effect of Basal Promoter Sequence

Although removal of nls greatly improved the ability of cumate to turn off expression, the off state of the switch was higher than expected. Ideally, expression in the off state should be no higher than that seen in mock-transfected cells. However, even if cumate is able to completely turn off any transativator-dependent activation, the basal expression of the minimal promoter elements will still be present. It is important therefore to have TATA sequences that are only minimally active in the absence of transactivation. To determine whether the minimal promoter elements of the CMV immediate early gene meets the requirements of such a TATA sequence, reporter activity was measured and compared to that of cells transfected with only the seap plasmid. Using the calorimetric assay, no significant difference was detected. However both values are very close to the limit of detection of that method. Therefore a more sensitive method of detection using a luminescent substrate of β-gal was used. With this method it was clear that the CMV minimal promoter is very active in 293 cells (40 fold over mock/seap transfected cells) (Table 2). Minimal promoter elements from other genes were therefore tested in the same assay.

TABLE 2

| | Basal Promoter Activity | | |
|---|---|---|---|
| | Colorimetric | Luminometric Assay | |
| Sample | Assay | β-gal/seap | Fold increase |
| Mock | 0.014 | 0.15 | |
| CMV min. | 0.036 | 6.08 | 40 |
| VIP | 0.019 | 0.55 | 3.5 |
| Tk | 0.019 | 0.43 | 2.7 |
| HSP | 0.026 | 2.93 | 18.7 |
| MLP | 0.019 | 0.779 | 4.9 |
| MMTV | 0.023 | 1.079 | 6.8 |

Table 2 shows the result of such a test. The HSP promoter (pAdCR9LacZ) has the next highest activity in 293 cells (18.7 fold over control). TATA sequences from vip, hsv-tk, Adeno MLP and MMTV (pAdCR10LacZ, pAdCR6LacZ, pAdCR7LacZ and pAdCR8LacZ respectively) are all between 3-6 fold over the control. The CMV minimal promoter was therefore replaced with each of these different elements and tested as reporters for the gene-switch. When the test was done using a calorimetric assay, although no significant difference was seen in the basal activity of the reporter activity, in the presence of the transactivator, clear differences in the level of activated expression were seen (CMV>HSP>MLP=MMTV>tk=vip) (FIG. 6). Moreover these differences were paralleled by differences in the off levels in the presence of cumate. When the same experiment was analyzed using a luminescent substrate, differences in basal activity of the reporter were evident (Table 3). All the configurations of the reporter construct were activated 150-300 fold over their respective basal levels. Therefore when compared with respect to the absolute activated levels, the CMV minimal promoter is the highest and that of vip and tk are the lowest. They were also all repressed 3-5 fold on the addition of cumate, making tk and vip modifications the least leaky in terms of absolute levels of off expression and CMV, the most leaky.

TABLE 3

Effect of Basal Promoter Sequence (293)

| Sample | P1 | P1 + Activator Cumate − | Cumate + | Fold Activation | Fold Repression |
|---|---|---|---|---|---|
| Mock | 0.15 | | | | |
| CMV | 6.08 | 1327.8 | 403 | 218 | 3.28 |
| VIP | 0.55 | 88.1 | 21.1 | 159 | 4.16 |
| Tk | 0.43 | 76.1 | 22.2 | 176 | 3.42 |
| HSP | 2.93 | 852.6 | 186.1 | 293 | 4.58 |
| MLP | 0.779 | 215.9 | 36.4 | 275 | 5.92 |
| MMTV | 1.079 | 195.3 | 64.6 | 181 | 3.02 |

Transfection in HeLa

Figure 7A:
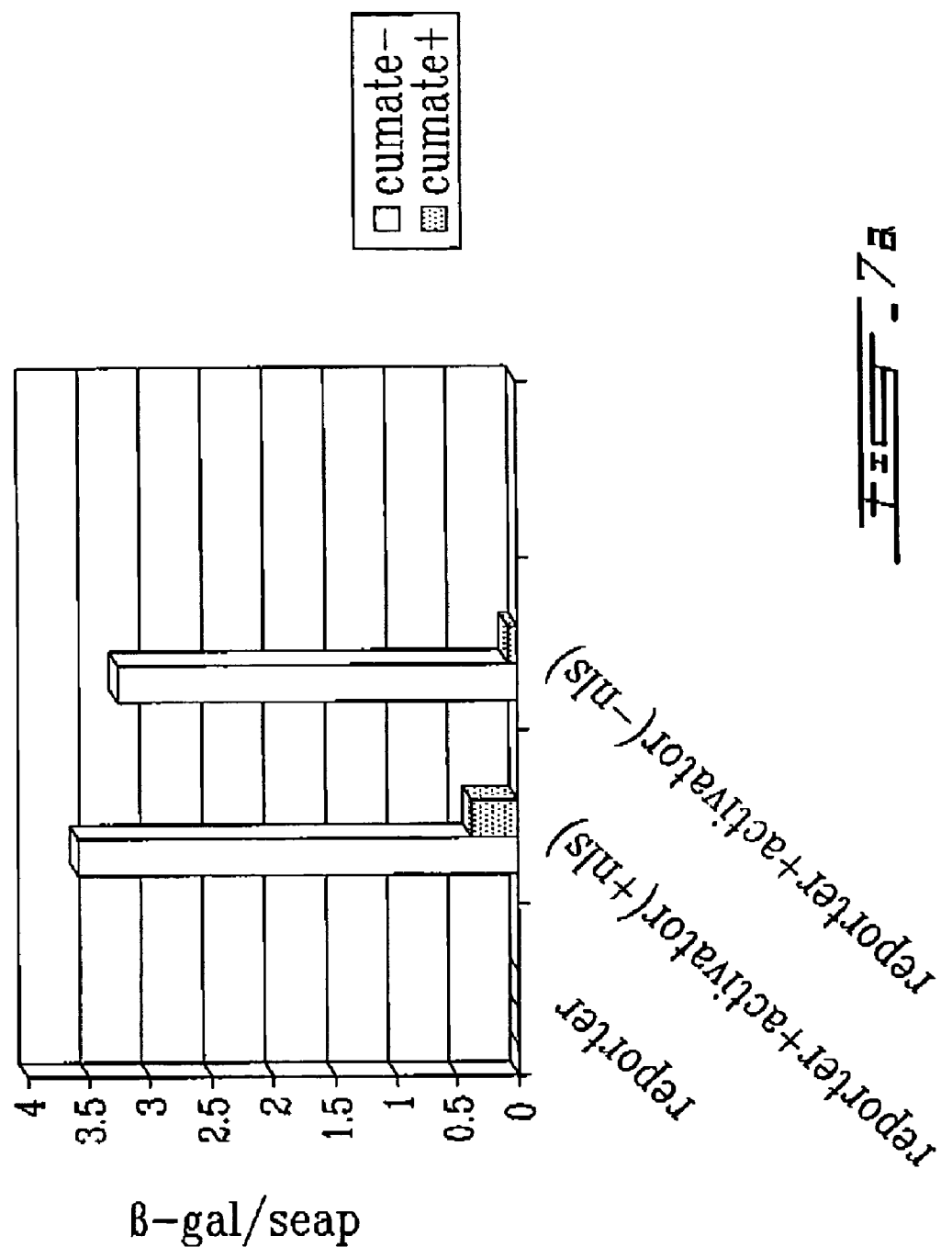
FIG. 7A is a graph representing the effect of nuclear localization signal (HeLa cells)

Reporter and activator constructs were co-transfected into HeLa cells as described previously. FIGS. 7A and 7B show the results of a typical experiment. The reporter construct (pAdCR5LacZ), when transfected alone produced minimal amounts of β-gal activity. On co-transfection with the plasmid coding for the transactivator (pAdcTA1(+nls)), however, there was a large increase in the activity of β-gal activity. Addition of cumate to the medium caused a 9.4 fold decrease in the activation by the transactivator. (FIG. 7B).

Effect of nls

As in the case of 293 cells, deletion of the nls sequence (pAdcTA1(−nls) had no effect on the ability of the activator to activate transcription. In the presence of cumate, however, the reduction in activation was more efficient (34-fold reduction of the levels seen in the presence of cumate) (FIG. 7B).

Transfection in BMAdE1/78-42

Figure 8:
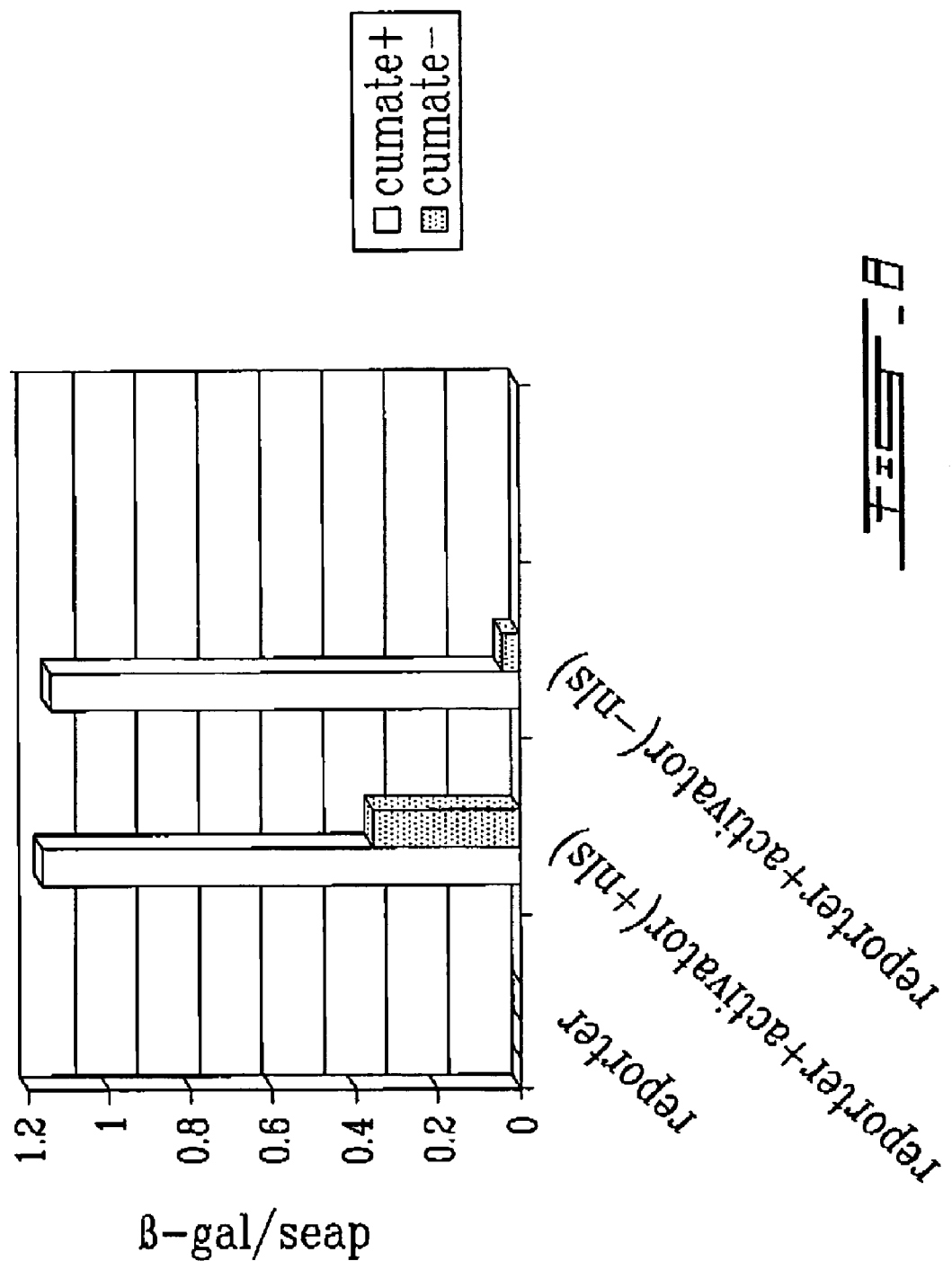
FIG. 8 is a graph representing the effect of nuclear localization signal (BMAdE1/78-42)

Reporter and activator constructs were co-transfected into BMAdE1/78-42 cells as described previously. FIG. 8 shows the results of a typical experiment. The reporter construct (pAdCR5LacZ), when transfected alone produced minimal amounts of β-gal activity. On co-transfection with the plasmid coding for the transactivator (pAdGTA1(+nls)), however, there was a 150-fold increase in the activity of β-gal activity. Addition of cumate to the medium reduced the activation by 3.9 fold.

Effect of nls

As in the case of 293 cells, deletion of the nls sequence (pAdcTA1(−nls) had no effect on the ability of the activator to activate transcription. In the presence of cumate, however, the reduction in activation was more efficient (a 22-fold reduction of the levels seen in the presence of cumate).

The Cumate Switch in a Stable Expression System

The expression plasmid for the cumate activator (pMPG-cTA-tk-neo-nls) comprises of three independent expression cassettes, one for the expression of the cumate transactivator driven by the CMV5 promoter, a second one for BFPq expression driven by the CMV promoter and a third one for the expression of the protein conferring resistance to G418 (neo). It was derived from the pMPG series of vectors described in Gervais et aL. (Gervais et al. in K. Nagai and M. Wachi eds. Animal Cell Technology: Basic and Applied Aspects, vol. 9, Kluwer Academic Publishers, Dordrecht, The Netherlands, 1998 pp 349-354).

$1 \times 10^6$ CHO cells were transfected with 5 μg of pMPG-cTA-tk-neo-nls using 12 μl of LIPOFECTAMINE 2000 according to the instructions of the manufacturer. 1200 μg/ml G418 was added to the growth medium 48 h after transfection to select a pool of G418-resistant cells. Individual clones (CHO-cTA) were isolated from this pool by the method of limiting dilution.

Adenoviral Infection of CHO-cTA Clones

CHO-cTA clones were infected with AdCMV5GFPq or AdCR5GFPq at MOIs of 100, 300 and 900 in the presence or absence of 200 μg/ml cumate. Forty-eight hours post-infection, cells were fixed in 2% paraformaldehyde in PBS. Total GFP fluorescence of the infected population was measured using an EPICS-XL flow cytometer (Coulter).

Results

Several CHO-cTA clones were tested by infection of AdCR5-GFPq in the presence and absence of cumate. Cells were also infected with AdCMV5-GFPq as a control virus. Forty-eight hours post infection cells were fixed and total GFP fluorescence was measured. On infection with AdCR5-GFPq (MOI of 100, 300 and 900) there is a 1728, 5578 and 9476-fold increase in activity over mock infected cells. Addition of cumate reduced GFP expression to 2, 4.5 and 20.6-fold over those in mock infected cells. The ON levels of the cumate switch are marginally higher than those generated by infection of the control virus, AdCMV5-GFPq (813, 2374 and 7661-fold over mock infected cells at MOIs of 100, 300 and 900 respectively.

EXAMPLE II

Strategy 2

Components of the Switch

The Repressor

The repressor is the cumate repressor CymR as found in recombinant plasmid pTNP-47.

The Reporter Construct

The reporter construct consists principally of three components: the CymR binding site (operator sequence, see FIG. 1), the basal promoter element and a reporter gene (β-galactosidase) such that the operator sequence is inserted downstream of the start site. (FIG. 3).

293 Cells

Figure 9:
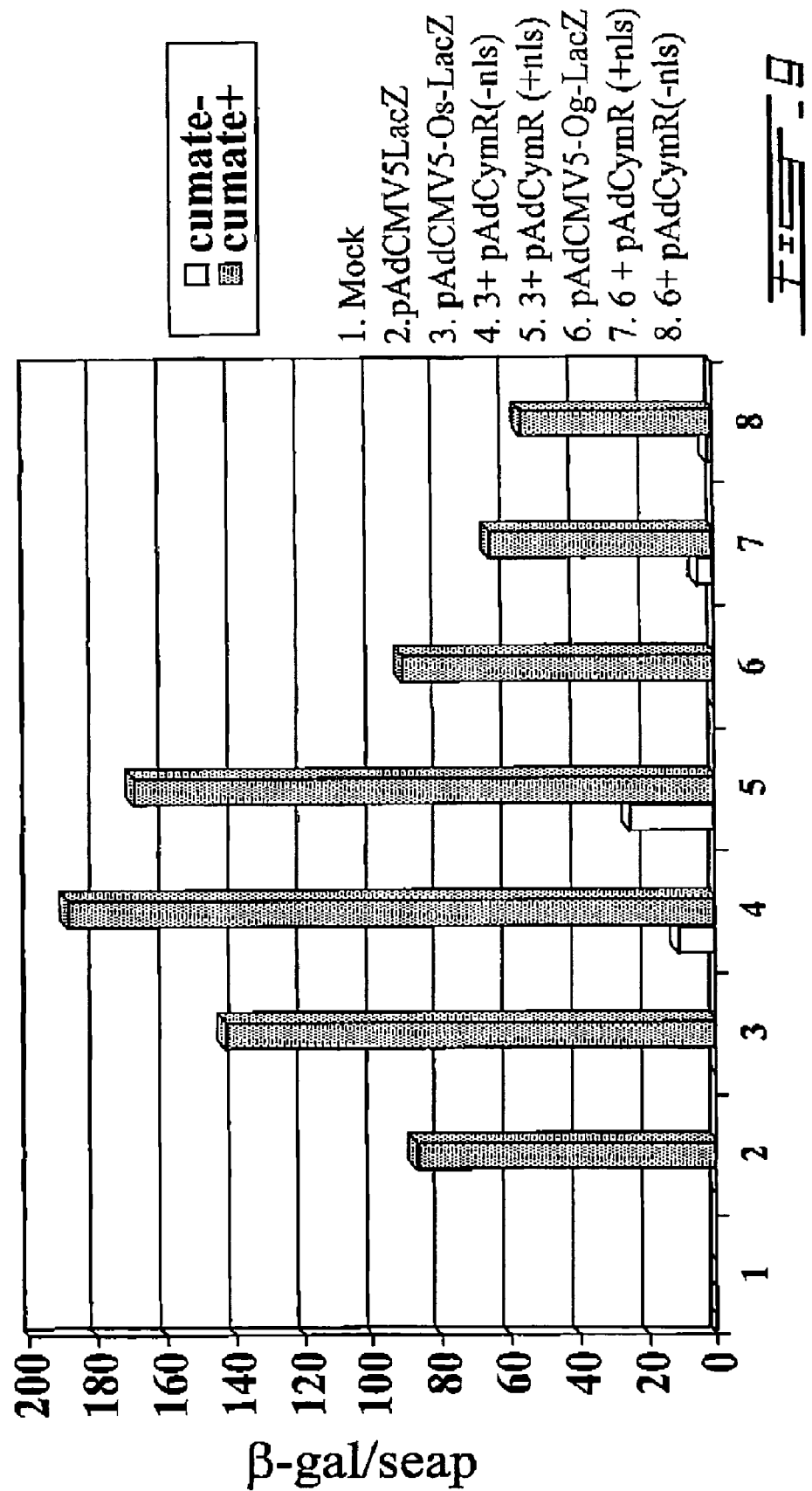
FIG. 9 is a graph representing CymR-mediated repression.

When 293 cells were transfected with 5 μg of either pAdCMV5-Og-LacZ or pAdCMV5-Os-LacZ on their own, both vectors expressed reporter activity comparable to that of from an unmodified CMV5 promoter. Expression from the pAdCMV5-Os-LacZ construct is actually slightly higher (165%) than that from the CMV5 construct. Expression from the pAdCMV5-Og-LacZ construct is indistinguishable from that of the CMV5 control. Co-transfection of 0.25 μg of repressor plasmid (pAdcymR) reduced expression from both the pAdCMV5-Os-LacZ and the pAdCMV5-Og-LacZ constructs by 93% and 94.2% respectively. Furthermore, addition of cumate relieved the repression totally in both cases (FIG. 9). The repressor construct containing the nls (pAdCymR(−nls)) was less efficient in blocking transcription (83%) from the pAdCMV5-Os-LacZ reporter, although addition of cumate relieved the repression completely. In case of the pAdCMV5-Og-LacZ reporter, the nls containing repressor was just as efficient (as the repressor without the nls) in blocking repression (95%), but addition of cumate did not relieve the repression completely. Only 61% of the activity in the unrepressed state was recovered.

Testing of Viral Stock

Figure 10:
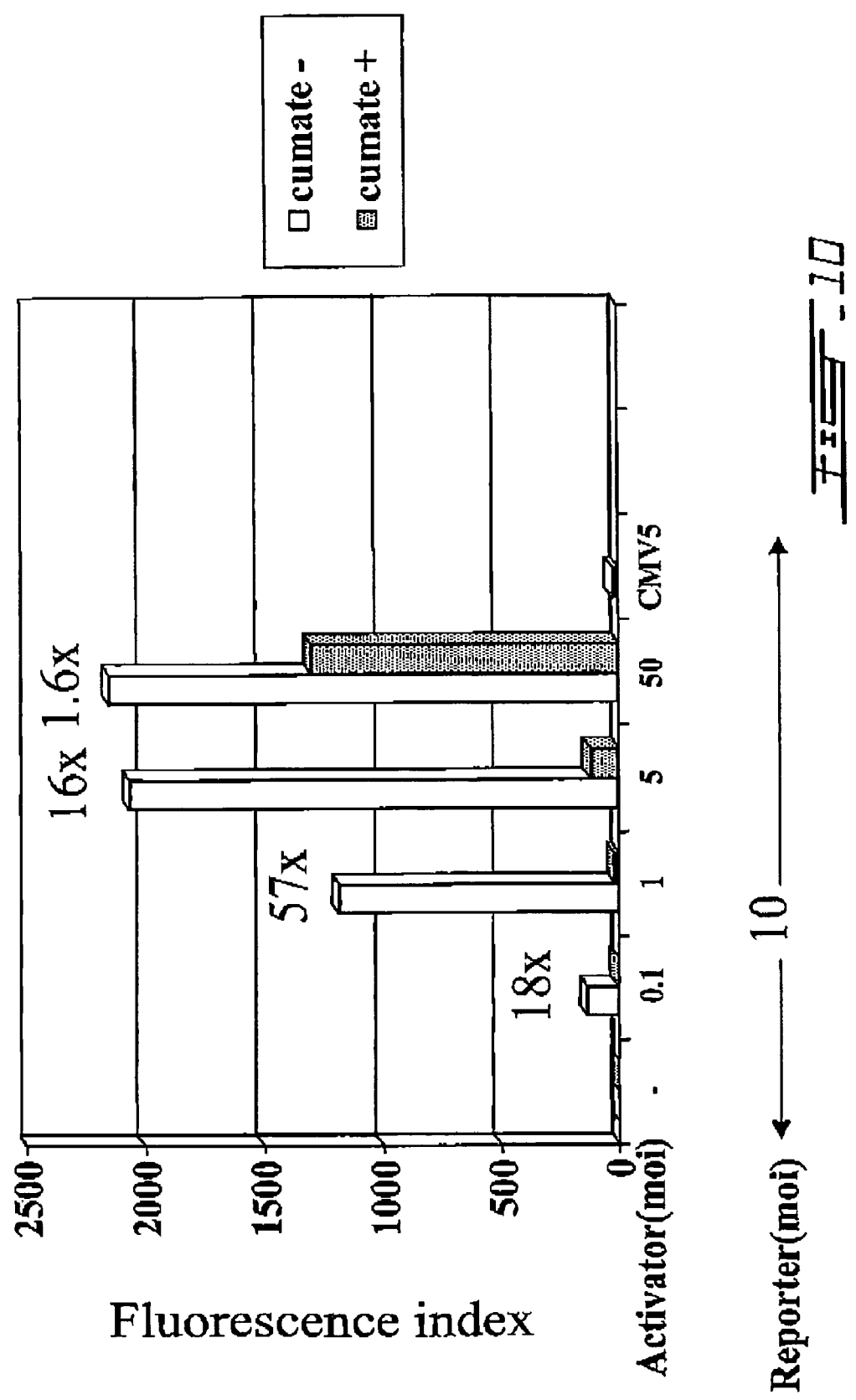
FIG. 10 is a graph representing the cumate switch of the present invention in rAd vectors.

Recombinant adenoviral constructs were generated for both reporter (pAd CR5' GFP) and activator (pAd Cu2-nls) transfer vectors. Viruses were purified and amplified. A co-infection strategy was used to test the system. The reporter construct was used at mois of 10 and 50. For each of the two mois, the activator virus was added at mois of 0.1, 1, 5 and 50. As is seen in FIG. 10, with the reporter being used at a moi of 10, co-infection with very small amounts of activator (moi 0.1) resulted in a large increase (1000 fold) in reporter activity. 95% of this increase could be obliterated by the addition of cumate. Ten times more activator (moi 1) resulted in approximately 10 fold higher activation. 98% of this increase could be obliterated by the addition of cumate. At higher mois of activator (moi 5) it is clear that the system is at saturation. Five times more activator does not result in 5 times better activation. Furthermore the activation at a mol of 50 for the activator virus is not significantly higher than that at 5.

Figure 11:
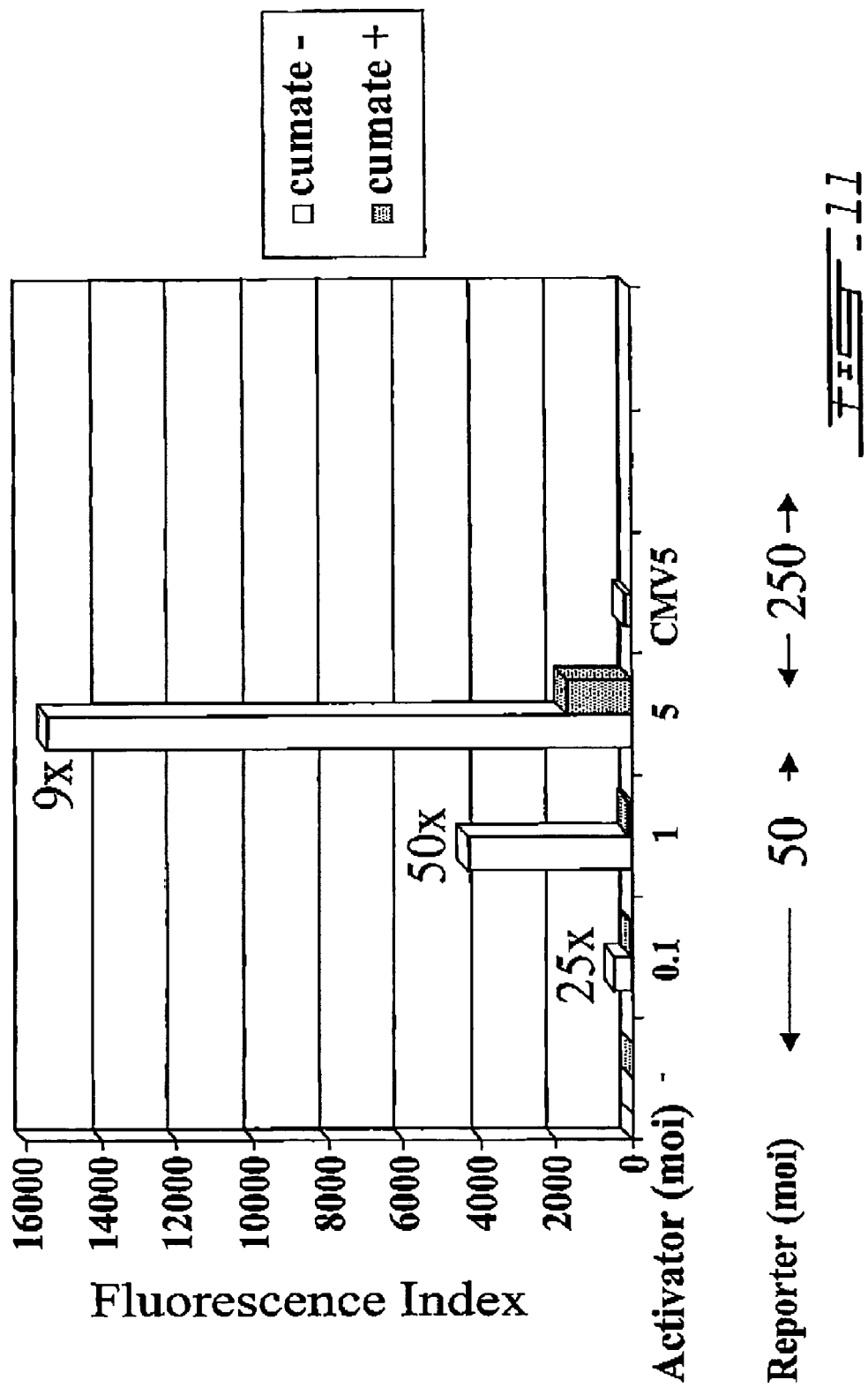
FIG. 11 is a graph representing the cumate switch of the present invention in rAd vectors.
Figure 17:
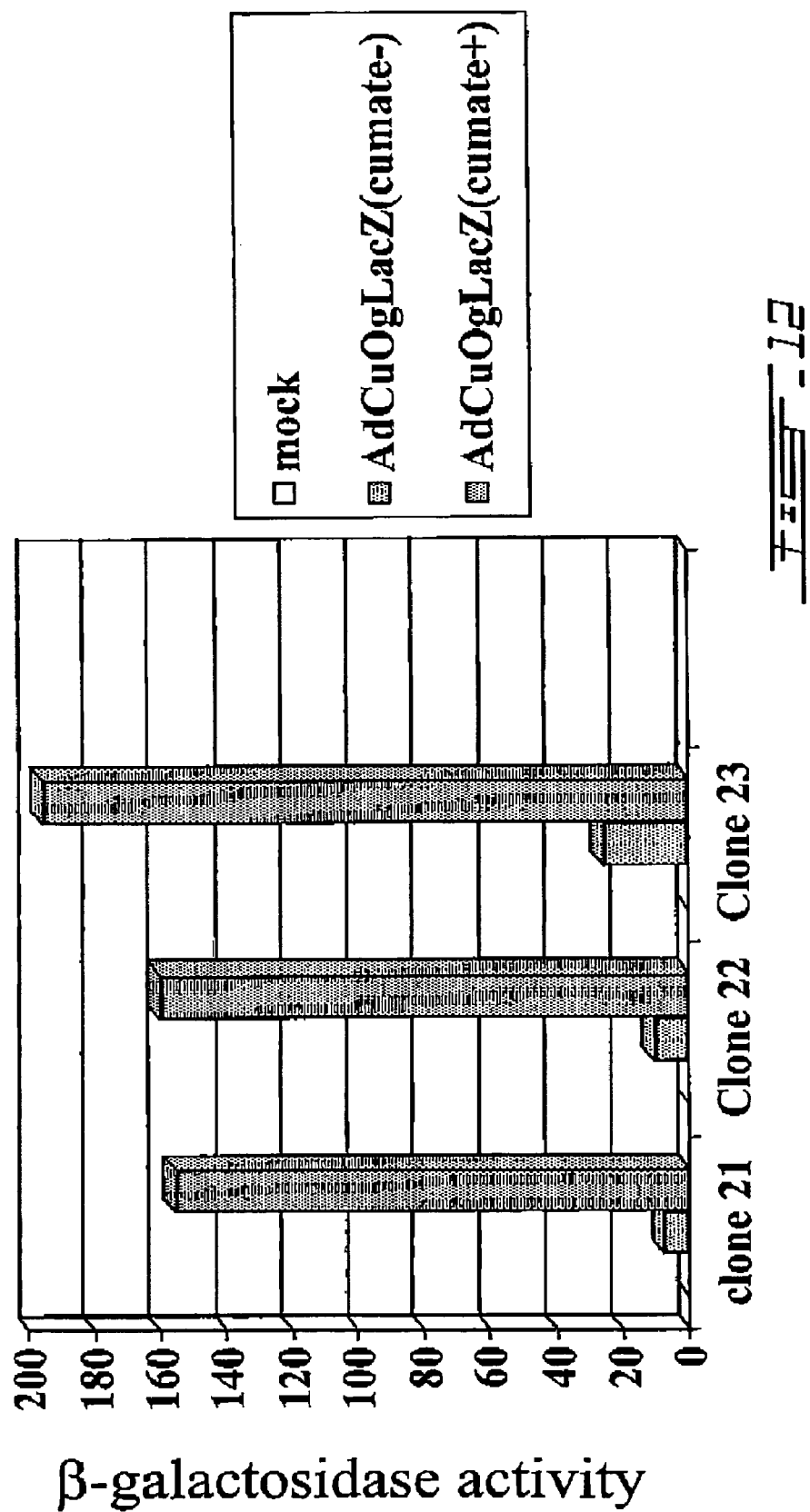

When the experiment is performed using a higher moi for the reporter (moi 50), essentially the same result is obtained (FIG. 11). At low activator mois strong activation is observed and this activation is efficiently reduced by the addition of cumate. The system is saturated for activation at higher mois of the activator virus.

293-CymR $1 \times 10^6$ 293 cells were transfected with 10 μg of pCymR/tk-neo by the calcium phosphate technique. 400 μg/ml G418 was added to the growth medium 48 h after transfection to select a pool of G418-resistant cells. Individual clones (293-CymR) were isolated from this pool by the method of limiting dilution.

Adenoviral Infection of 293-CymR Clones

293CymR clones were infected with AdCMV5-Og-LacZ in the presence and absence of 200 μg/ml cumate. β-galactosidase activity was measured 48 h post-infection.

Western Blot Analysis

8 μg of pAdCMV5-CuO-VSVg was transfected into $1 \times 10^6$ 293-CymR clone 21 cells using the calcium phosphate technique in the presence and absence of 200 μg/ml cumate. Forty-eight hours post transfection cells were lysed in Laemli buffer. Western analysis was performed using standard techniques and probed with a mouse monoclonal anti-VSVg antibody (Gibco clone P5D4). Antibody binding was visualized using an ECL detection kit (Amersham).

The expression plasmid for VSVg (pAdCMV5-CuO-VSVg) is a dicistronic plasmid where the expression of VSVG and BFPq are controlled by the repressible cumate promoter. The VSVg coding sequence was cloned as a BgIII fragment in the BamHI cloning site of pAdCMV5-CuO-DC-BFPq. pAdCMV5-CuO-DC-BFPq was constructed by replacing the promoter fragment (HpaI-XhoI) of pAdTR5-DC-GFPq (2) with that from pAdCMV5-CuO-GFPq. pAdCMV5CuO-GFPq was generated by replacing the BamHI-XhoI fragment of pAdCMV5-CuO-LacZ with that of pAdCMV5GFPq (Massie, B., et al., *Cytotechnology*, 28, 53-64, 1998).

293-CuO-GFPq $1 \times 10^6$ 293-CymR clone 21 were transfected with 10 μg of pAdCMV5-CuO-GFPq. GFP expression was induced by the addition of 200 μg/ml cumate and individual GFP positive cells were picked by Quixell™ (Caron, A. W., et al., Methods in cell science 22: 137-145, 2000).

Results

Adenoviral Infection of 293-CymR Clones

Several 293-CymR clones were tested by infection of AdCMV5-Og-LacZ in the presence and absence of cumate. Forty-eight hours post infection cell extracts were prepared and β-gal activities were measured. FIG. 12 shows the results of three clones. On infection with AdCMV5-Og-LacZ, there is a small but detectable increase in β-gal activity, clone 21 being the lowest of the three. Addition of cumate results in a marked increase in activity, clone 23 being the highest of the three. The ON/OFF ratio for clones 21, 22 and 23 are 19, 16 and 7.6 respectively.

293-CymR Clone 21 can be Used to Generate a rAd Expressing a Toxic Protein

To generate a rAd expressing a toxic protein it is crucial that expression of the toxic protein be minimal during the time required for viral generation and propagation. Since the first step involves co-transfection of transfer vector and viral DNA, the expression of VSVg from pAdCMV5-CuO-VSVg in 293-CymR clone 21 was verified. Forty eight hours post-transfection, cell extracts were prepared and subjected to western analysis using antiVSVg antibodies FIG. 13 shows that in VSVg expression is undetectable in the absence of cumate. On addition of cumate, VSVg expression is clearly evident.

The generation of a rAd expressing VSVg using this system was therefore undertaken. Purified virus was used to infect 293-CymR in the presence and absence of cumate. The infected cells were photographed at a magnification of 25×. FIGS. 14A and 14B show that addition of cumate induces the expression of VSVg and the infected cells form syncitia, a characteristic effect of VSVg expression. In the absence of VSVg induction however, 293-CymR cells exhibit the morphology typical of cells infected with adenovirus. No syncitium formation is evident, indicating low or no VSVg expression.

Tight Control of Expression from a Stably Integrated Plasmid

Figure 15A:
FIGS. 15A to 15C represent GFP expression in the presence (FIG. 15A) of cumate, in absence of cumate or in the OFF state (FIG. 15B) and with phase contrast in the OFF state (FIG. 15C)
Figure 15B:
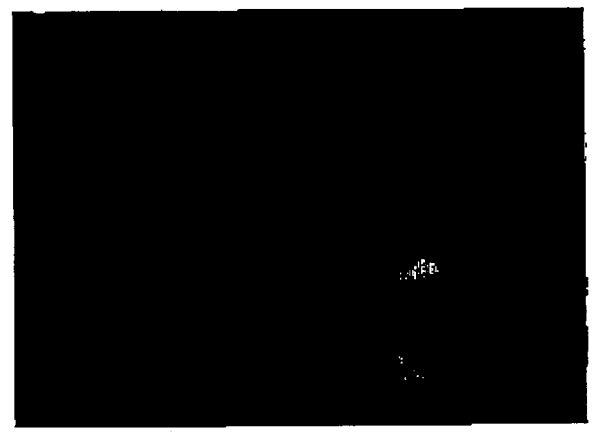
Figure 15C:
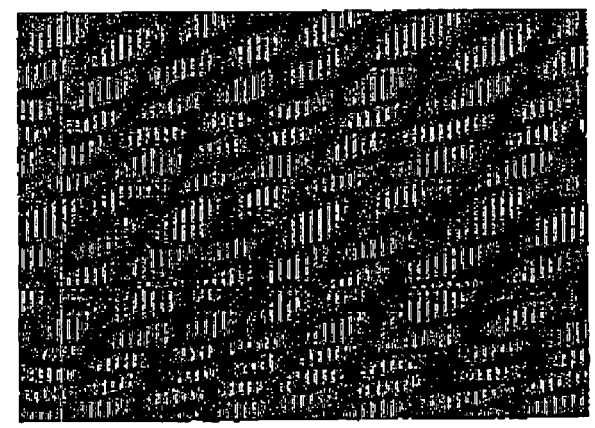

To determine whether expression of a reporter gene can be tightly controlled from stably integrated sequences, a plasmid expressing GFPq from a cumate-repressible promoter (pAdCMV5-CuO-GFPq) was stably integrated into 293-CymR clone 21 cells. Several clones were isolated and tested. FIGS. 14A and 14B show the results of one of the clones (293-CuO-GFPq13#):

293-CuO-GFPq13# were cultured in the presence and absence of cumate for 48 h. Photographs were taken using an inverted fluorescence microscope (Leica, Wetzlar, Germany). FIGS. 15A to 15C show that 100% of cells are positive for GFP expression in the presence (FIG. 15A) of cumate. In the OFF state (FIG. 15B) only two GFP-positive cells are visible in the microscopic field. The phase contrast image of FIG. 15B (FIG. 15C) demonstrates the presence of cells in the microscopic field.

Total GFP fluorescence was measured in the ON (9255) and OFF (3.75) states using an EPICS-XL flow cytometer (Coulter). The ON/OFF ratio for this clone was 246.

Figure 16:
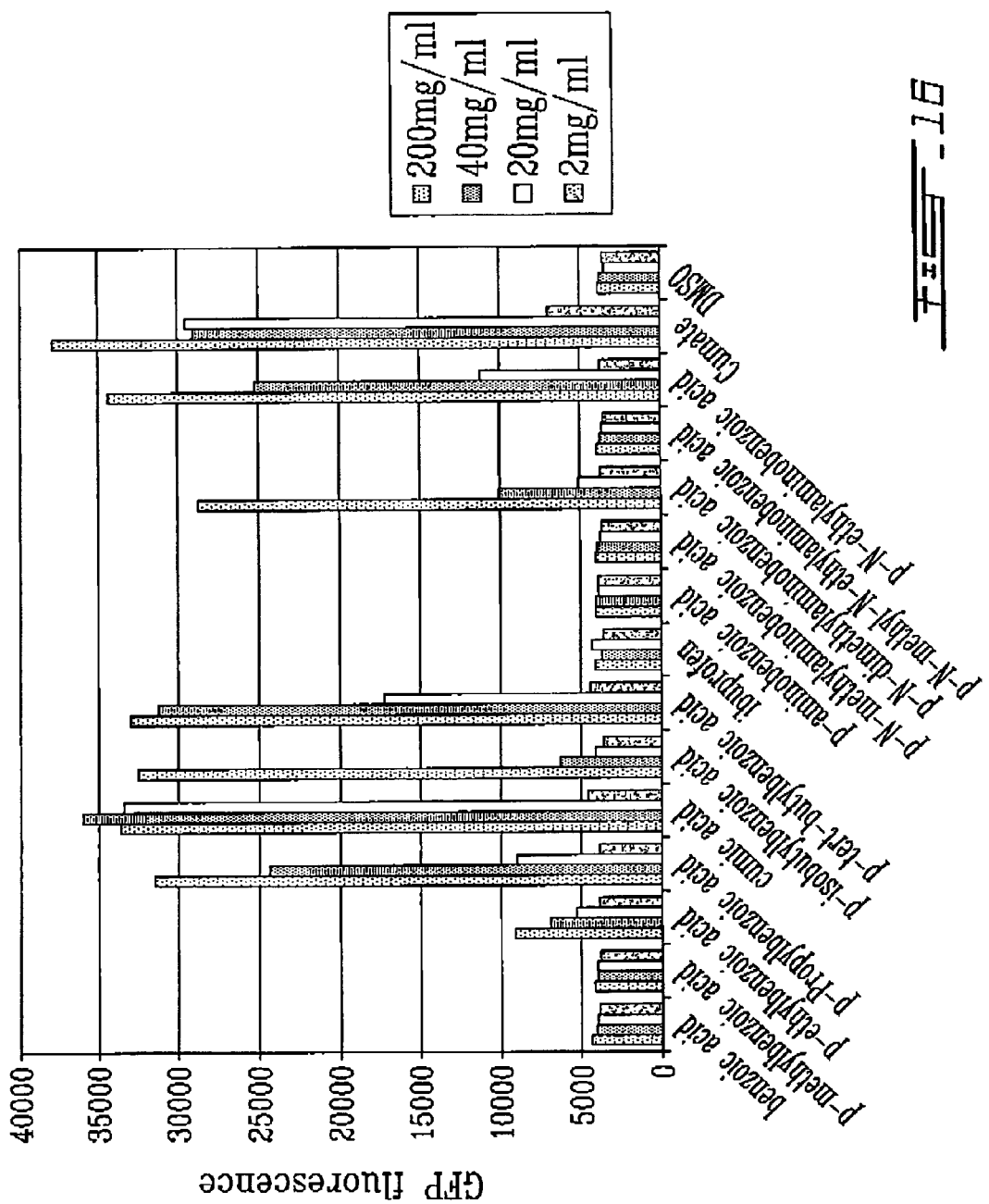
FIG. 16 illustrates the results obtained for the testing of various cumate analogues that can be used as effector molecule.

Of course cumate can be substituted for various cumate analogues also referred to as effector molecule as described before. FIG. 16 illustrates that p-Propylbenzoic acid (referred to as C4), cumic acid (referred to as C5), p-isobutylbertzoic acid (referred to as C6), p-tert-butylbenzoic acid (referred to as C7), p-N-dimethylaminobenzoic acid (referred to as C11), and p-N-ethylaminobenzoic acid (referred to as C13) are good activator (see FIG. 16).

In conclusion therefore, two different strategies for the construction of a new inducible system and modifications of the system that are optimal for different kinds of applications have been described. It has been demonstrated that the system of the present invention is able to control gene expression very effectively in different mammalian cells.

Deposits

Table 4 includes, pursuant to Rule 7.1 of the Budapest Treaty Regulations the details of the Deposit of various DNA samples within the international Depository Authority of Canada, 1015 Arlington Street, Winnipeg, Manitoba, Canada, R3E 3R2. The Deposits were received by the authority on 29 Mar. 2001, and were tested and found viable on 30 Mar. 2001.

TABLE 4

DNA Samples

| Sample Number | Name of Deposit | Accession Number |
| --- | --- | --- |
| 1 | PAd cTA1(-nls) | IDAC 290301-1 |
| 2 | PadCR5LacZ | IDAC 290301-2 |
| 3 | PadCR5'LacZ | IDAC 290301-3 |
| 4 | PadCR5'GFP | IDAC 280301-4 |
| 5 | PAdCMV5-Os-LacZ | IDAC 290301-5 |
| 6 | PAdCMV5-Og-LacZ | IDAC 290301-6 |
| 7 | PAdCymR(-nls) | IDAC 290301-7 |

Table 5 includes the details of the Deposit of various Adenovirus Vector Samples. The Deposits were received by the authority on Apr. 5, 2001 and were tested and found viable on Apr. 17, 2001.

TABLE 5

Adenovirus Vector Samples

| Sample Number | Name of Deposit | Accession Number |
| --- | --- | --- |
| 1 | AdCR5'GFP | IDAC 050401-1 |
| 2 | AdCTA2(-nls) | IDAC 050401-2 |

Other deposits have been relating to CHO cells expressing the cumate transactivator (designated CHO.S-cta 10D11 and CHO.S-cta 10H11), and to 293 cells (exemplifying strategy 2) stably integrating the cumate transactivator, used to test cumate analogues (designated 293 CuO-GFP clone 13). CHO.S-cta 10D11 and CHO.S-cta 10H11 have been deposited within the International Depository Authority of Canada, 1015 Arlington Street, Winnipeg, Manitoba, Canada, R3E 3R2. The Deposits were received by the authority on Apr. 10, 2002, and were given accession number IDA-100402-1 and IDA-100402-2, respectively. 293 CuO-GFP clone 13 was also deposited on Apr. 10, 2002 in the same IDA and was given accession number IDA-100401-3.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated recombinant DNA molecule comprising:
   a) a mammalian promoter sequence having a TATA element;
   b) an operator sequence selected from the group consisting of P1 and P2 operator sequences positioned 3' to the start of the transcription site, said P1 and P2 operator sequences consisting of SEQ ID NO:1 and SEQ ID NO:2, respectively; and
   c) the coding sequence of a gene lying 3' to said operator and operably linked to said promoter.

2. The DNA molecule of claim 1, wherein said promoter is selected from the group consisting of CMV, VIP, tk, HSP, MLP, and MMTV promoters.

3. A host cell transformed with a vector comprising the DNA molecule of claim 1.

4. A method for producing recombinant protein in a mammalian cell making the CymR repressor protein of *Pseudomonas putida*, said method comprising:
   a) transforming said mammalian cell in vitro with a vector comprising:
      (i) a mammalian promoter sequence having a TATA element;
      (ii) an operator sequence selected from the group consisting of P1 and P2 operator sequences positioned 3' to the start of the transcription site, said P1 and P2 operator sequences consisting of SEQ ID NO:1 and SEQ ID NO:2, respectively; and
      (iii) the coding sequence of a gene lying 3' to said operator and operably linked to said promoter wherein the coding sequence of said gene encodes said recombinant protein;
   b) introducing an effector molecule that regulates CymR-mediated expression into the transformed cells of step a) to induce the expression of said gene and produce said recombinant protein, said effector molecule being selected from the group consisting of p-ethylbenzoic acid, p-propylbenzoic acid, cumic acid, p-isobutylbenzoic acid, p-terbutylbenzoic acid, p-N-dimethylaminobenzoic acid, p-N-ethylaminobenzoic acid and cumate.

5. The method of claim 4, wherein said promoter is selected from the group consisting of CMV, VIP, tk, HSP, MLP, and MMTV promoters.

6. The method of claim 4, wherein said effector molecule is selected from the group consisting of cumate, Di-methyl p-aminobenzoic acid (DM PABA), and p-ethylbenzoic acid, or a salt thereof.

7. An isolated recombinantly engineered virus comprising within its genome:
   a) a recombinant promoter having a TATA element;
   b) an operator sequence selected from the group consisting of P1 and P2 operator sequences positioned 3' to the start of the transcription site, said P1 and P2 operator sequences consisting of SEQ ID NO:1 and SEQ ID NO:2, respectively; and
   c) the coding sequence of a gene lying 3' to said operator and operably linked to said promoter, wherein the coding sequence of said gene inhibits the replication of said virus when expressed.

8. The virus of claim 7, wherein said promoter is selected from the group consisting of CMV, VIP, tk, HSP, MLP, and MMTV promoters.

9. A host cell made by infecting a cell in vitro with the virus of claim 7.

10. An isolated recombinant DNA molecule comprising:
    a) a mammalian promoter sequence having a TATA element;
    b) at least one operator sequence selected from the group consisting of P1 and P2 operator sequences positioned 5' to the TATA element, said P1 and P2 operator sequences consisting of SEQ ID NO:1 and SEQ ID NO: 2, respectively; and
    c) a gene lying 3' to the TATA element and operably linked to the promoter.

11. An isolated recombinantly engineered virus comprising within its genome the recombinant DNA molecule of claim 10.

12. The virus of claim 11, wherein said promoter is selected from the group consisting of CMV, VIP, tk, HSP, MLP, and MMTV promoters.

13. A host cell made by infecting a cell in vitro with the virus of claim 11.

14. An isolated recombinant DNA molecule comprising:
    a) a mammalian promoter; and
    b) the coding sequence of CymR-VP16 cumate activator operably linked to the promoter.

15. An isolated recombinantly engineered virus comprising within its genome the recombinant DNA molecule of claim 14.

16. A host cell transformed in vitro with a vector comprising the recombinant DNA molecule of claim 14.

* * * * *